(12) United States Patent
Makrigiorgos

(10) Patent No.: US 7,452,699 B2
(45) Date of Patent: Nov. 18, 2008

(54) AMPLIFICATION OF DNA IN A HAIRPIN STRUCTURE, AND APPLICATIONS

(75) Inventor: G. Mike Makrigiorgos, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 340 days.

(21) Appl. No.: 10/758,401

(22) Filed: Jan. 15, 2004

(65) Prior Publication Data
US 2005/0142559 A1 Jun. 30, 2005

Related U.S. Application Data

(60) Provisional application No. 60/440,184, filed on Jan. 15, 2003.

(51) Int. Cl.
*C12P 19/34* (2006.01)
(52) U.S. Cl. .................................................. 435/91.2
(58) Field of Classification Search .................. None
See application file for complete search history.

(56) References Cited

U.S. PATENT DOCUMENTS

| | | | | |
|---|---|---|---|---|
| 5,470,724 | A * | 11/1995 | Ahern | 435/91.2 |
| 6,114,115 | A * | 9/2000 | Wagner, Jr. | 435/6 |
| 6,235,502 | B1 * | 5/2001 | Weissman et al. | 435/91.1 |
| 7,208,278 | B2 * | 4/2007 | Chen et al. | 435/6 |
| 2003/0108902 | A1 * | 6/2003 | Abarzua | 435/6 |

OTHER PUBLICATIONS

Liu, Q. et al., "Truncated Amplification: A method for High-Fidelity Template-Driven Nucleic Acid Amplification," Biotechniques, Jul. 2002, vol. 33, pp. 129-138.*
James et al., "Surprising fidelity of template-directed chemical ligation of oligonucleotides," Chemistry and Biology, 1997, vol. 4, pp. 595-605.*
Paulo Andre et al., "Fidelity and Mutational Spectrum of Pfu DNA Polymerase on a Human Mitochondrial DNA Sequence," Genome Research, vol. 7, p. 843-852, (1997).
Bartram, C.R. et al, "Detection of minimal residual leukemia by polymerase chain reactions," Bone Marrow Transplant, p. 4-8, (1990).
Neal F. Cariello et al., "Fidelity of Thermococcus litoralis DNA polymerase (Vent) in PCR determined by denaturing gradient gel electrophoresis," Nucleic Acids Research, vol. 19 ( No. 15), p. 4193-4198, (Jul. 1, 1991).
Aimee L. Jackson et al., "On the origin of multiple mutations in human cancers," Seminars in Cancer Biology, vol. 8, p. 421-429, (1998).
Gareth J.S. Jenkins et al., "Mutation analysis using the restriction site mutation (RSM) assay," Mutation Research, vol. 405, p. 209-220, (1998).

(Continued)

*Primary Examiner*—Kenneth R. Horlick
*Assistant Examiner*—Molly E Baughman
(74) *Attorney, Agent, or Firm*—Fish & Richardson P.C.

(57) ABSTRACT

The present invention is directed to a hairpin nucleic acid structure and its use. In a preferred embodiment, the hairpin nucleic acid structure can be used in a method of amplification of a template nucleic acid sequence that substantially reduces polymerase-induced errors.

10 Claims, 14 Drawing Sheets

OTHER PUBLICATIONS

Manjit Kaur et al., "Ligation of a primer at a mutation: a method to detect low level mutations in DNA," Mutagenesis, vol. 17 (No. 5), p. 365-373, (2002).

Phouthone Keohavong, "Fidelity of DNA polymerases in DNA amplification," Proc. Natl. Acad. Sci. USA, vol. 86, p. 9253-9257, (Dec. 1989).

Konstantin Khrapko et al., "Mutational spectrometry without phenotypic selection: human mitochondrial DNA," Nucleic Acids Research, vol. 25 ( No. 4), p. 685-693, (1997).

Xiao-Cheng Li-Sucholeiki et al., "A sensitive scanning technology for low frequency nuclear point mutations in human genomic DNA," Nucleic Acids Research, vol. 28 ( No. 9), p. E44, (2000).

Qiang Liu et al., "Truncated Amplification: A Method for High-Fidelity Template-Driven Nucleic Acid Amplification," BioTechniques, vol. 33 (No. 1) p. 129-138, (Jul. 2002).

Page B. McKinzie et al., "Prospects for applying genotypic selection of somatic oncomutation to chemical risk assessment," Mutation Research, vol. 489, p. 47-78, (2001).

Hisayoshi Nakazawa et al., "Relationship Between Chemcially Induced Ha-ras Mutation and Transformation of BALB/c 3T3 Cells: Evidence of Chemical-Specific Activation and Cell Type-Specific Recruitment of Oncogene in Transformation," Molecular Carcinogenesis, vol. 3, p. 202-209, (1990).

Barbara L. Parsons et al., "Genotypic selection methods for the direct analysis of point mutations," Mutation Research, vol. 387, p. 97-121, (1997).

Barbara L. Parsons et al., "Detection of Basepair Substitution Mutation at a Frequency of 1×10(−7) by Combining Two Genotypic Selection Methods, MutEx Enrichment and Allele-Specifi Competitive Blocker PCR," Environmental and Molecular Mutagenesis, vol. 32, p. 200-211, (1998).

H. Steingrimsdottir et al., "Development of new moleuclar procedures for the detection of genetic alterations in man," Mutation Research, vol. 353, p. 109-121, (1996).

Transgenomic, "Transgenomic Optimase Polymerase Delivers Highest Fidelity in PCR for Wave System Analysis," (US).http://www.transgenomic.com/pdf/AN119u.pdf, (2002).

David Sidransky, "Nucleic Acid-Based Methods for the Detection of Cancer," Science, vol. 278, p. 1054-1059, (Nov. 7, 1997).

Vincent L. Wilson et al., "Oncogenic Base Substitution Mutations in Circulating Leukocytes of Normal Individuals," Cancer Research, vol. 60, p. 1830-1834, (Apr. 1, 2000).

* cited by examiner

5' CTGCCGAGTTCCTGCTTTGAGATGCTGTGTTGAG
    ||||||||||
3' GACGGCTCAACCACAAGTTCCTATCAGCTGCA

```
5' ATTTAAATGTTTAAACACGCGGTGACTTAAACAGGCGCGCCCTTAACTAGTCGCCTTAG
    ||||||||||||||||||||||||||||||||||||||||||||||||||||||||||
3' GTACTAAATTTACAAATTTGTGCGCCACTGAATTGTCCGGCGGGAATTGAAAGTGCGATG
```

AMPLIFICATION OF DNA IN A HAIRPIN STRUCTURE, AND APPLICATIONS

CROSS-REFERENCE TO RELATED APPLICATIONS

This application claims benefit under 35 U.S.C. § 119(e) of U.S. Provisional Application No. 60/440,184, filed Jan. 15, 2003, which is incorporated herein by reference.

FIELD OF THE INVENTION

The present invention is directed to a hairpin nucleic acid structures and its use. In a preferred embodiment, the hairpin nucleic acid structure can be used in a method of amplification of a template nucleic acid sequence that substantially reduces polymerase-induced errors.

BACKGROUND OF THE INVENTION

Substantial interest has been directed to the detection of changes in nucleic acid sequences, such as caused by mutation and methylation. For example, mutation in certain genes have been associated with a variety of disorders-ranging from blood disorders to cancers. Genetic testing is one way to find this information out. However, our ability to detect such mutations is limited by certain problems with a key component in these tests, namely the polymerase chain reaction (PCR).

A major problem with PCR is that polymerases invariably generate errors during amplification. Such polymerase mis-incorporations can be indistinguishable from genuine mutations, and lower the quality of DNA cloning and protein functional analysis by in vitro translation. Polymerase mis-incorporations set a limit for molecular mutation detection methods: the most selective technologies invariably rely on PCR, but PCR also poses a final selectivity limit, typically 1 mutant in $10^5$-$10^6$ alleles, since all DNA polymerases generate errors during DNA synthesis which can be misinterpreted as mutations (false positives). Thus, high selectivity mutation detection technologies often fall short of the enormous selectivity needed to address issues like the generation of spontaneous mutations in somatic tissues[1,2], the early detection of genomic instability[3], the mutation screening of single cells[4] or the reliable detection of minimal residual disease[5,6]. Both unknown and known mutation detection methods are affected by PCR errors and the most selective methods are affected most.

For example, the principal limitation for mutation scanning via constant denaturant capillary electrophoresis (CDCE) is the fidelity of the polymerase used[7,8]. High selectivity mutation scanning via DGGE and dHPLC is ultimately hindered by polymerase error rate[7,9,10]. Some of the highest sensitivity assays for RFLP-based known mutation detection, including PCR/RE/LCR[11], MutEx-ACB-PCR[12], Radioactivity-based PCR-RFLP[13], RSM[14,15], APRIL-ATM[16], and others reviewed in Parsons et al.[17], utilize PCR in at least one stage prior to RFLP-selection, and are therefore also limited by PCR errors[18].

Accordingly, it would be desirable if one had a means of amplifying DNA free of polymerase-induced misincorporations, to detect mutations without being limited by polymerase-induced errors. This could significantly impact mutation detection, disease diagnosis, and cancer diagnosis.

SUMMARY OF THE INVENTION

We have now discovered compositions and methods to amplify a target nucleic acid sequence, sometimes referred to as the template, that substantially reduces polymerase induced errors in a sequence of interest, and which can supply existing technologies with the necessary 'selectivity leap'. The first step of this method involves converting the sequence of interest into a hairpin, which contains a double stranded region linked at one end through a single stranded loop, and performing PCR on the hairpin-structure. In the second step, the amplified PCR products are heat denatured and rapidly cooled, to convert each amplified PCR product into a hairpin: genuine polymorphisms or mutations will remain fully matched in the hairpin, whereas PCR products which contain a PCR induced error will form a hairpin that contains a mismatch in the double-stranded region. Thereafter, one removes those amplified nucleic acids which contain a mismatch by standard means. This method results in an amplified target nucleic acid which is substantially free of polymerase induced errors.

In an alternative embodiment, amplification of the hairpin structure is performed using isothermal rolling circle amplification (RCA).

True nucleic acid changes such as from a mutation can be separated from polymerase-generated single nucleotide changes, insertions, deletions, or slippage thereby providing practically error-less nucleic acid, preferably DNA. By using a hairpin sequence one can obtain a sample (template) from a range of sources such as from genomic DNA. Large fractions of the human genome can be amplified via hairpin PCR to provide faithfully—replicated genomic DNA for extensive, genome-wide screening for differences from a standard. This is particularly desirable when starting from limited amounts of biopsy material, i.e. from a few cells obtained via laser capture microdissection.

Additional technical factors limit the overall selectivity of mutation detection (e.g. amount of DNA; mis-priming; heteroduplex formation; incomplete enzymatic digestion[15]); however, with appropriate selection of conditions these problems can often be overcome. In contrast, PCR errors have been regarded as a 'glass ceiling' for mutation detection selectivity. The present method of using hairpin PCR will allow a boost to almost every existing method for highly selective mutation detection and lead to studies and diagnostic tests that were impossible with previous technology by substantially reducing the number of errors that are an artifact of PCR from the sample. This method will also improve microsatellite analysis by eliminating polymerase 'slippage' artifacts 19 and will also have application in other areas such as molecular beacons[20,21] and real time PCR, DNA cloning[22] or protein functional analysis by in vitro translation[4].

In one embodiment of the present invention, a hairpin with non-complementary ends can be efficiently PCR-amplified. In this embodiment, a target DNA sequence which needs to be PCR-amplified is first converted to a hairpin following ligation of an oligonucleotide 'cap' on one end and a pair of non-complementary linkers on the other end (See FIG. 1A). Next, primers corresponding to the two non-complementary linkers are used in a PCR reaction that proceeds by displacing the opposite strand and amplifying the entire complement of the hairpin.

In one preferred embodiment, these primers corresponding to the non-complementary linkers can overlap the sequence of interest, thus conferring sequence specificity. In this embodiment, exponential PCR amplification of the hairpin is enabled and sequences can be amplified directly from human genomic DNA. Following hairpin amplification, the PCR product is heat-denatured to allow the hairpins to separate from their complementary strand, and placed rapidly on ice. Because of the sudden cooling, cross-hybridization of different hairpins is minimal, and thus the original hairpins are reformed, following their amplification.

By amplifying DNA in a hairpin-formation, polymerase-errors practically always end-up forming a mismatch. Genuine mutations, however, remain fully-matched. For example, if the polymerase introduces an A>G mutation on the upper strand of the original sequence, it is very unlikely that, during synthesis of the bottom strand of a single hairpin it will perform the exact opposite error (T>C mutation) at exactly the complementary-strand position. This can be seen when one looks at the normal probability for such a double-error. Even for a polymerase with a large error rate of $10^{-4}$/base the odds for a double-error event are $10^{-4} \times 10^{-4} \times 0.25 = 2.5 \times 10^{-9}$, i.e. less than the expected spontaneous mutation rate in somatic tissues[1,24]. On the other hand, practically all genuine mutations remain fully matched following hairpin-PCR, as these reside in both strands from the beginning (FIG. 1A).

Preferably, the amplified hairpins that contain mismatches are efficiently separated from those that do not, using any procedure that recognizes mismatch. Preferred methods include dHPLC-mediated fraction collection and enzymatic based separation. Preferably, the hairpin caps are removed subsequent to the separation of hairpins containing mismatches from mismatch-free hairpins, thus allowing the original DNA sequence to be recovered. While the amplified DNA will have PCR-induced errors such errors can be removed from the amplified sample, which can now be processed for mutation detection without sensitivity being limited by polymerase errors.

In a further preferred embodiment, DGGE, dHPLC, as well as methods based on the mismatch-binding protein MutS or CelI or resolvases (endo V) or exomucleases are used to separate the fraction of PCR-amplified sequences containing polymerase errors[7, 10, 25-27]. These methods utilize the conversion of homoduplexes to heteroduplexes via cross-hybridization of PCR amplified products. Previously, both mutations and PCR errors are simultaneously converted to mismatches. When mutations are at a low frequency, practically all of them are converted to mismatches. Thus, such a means did not discriminate them from PCR errors. By the present method mutations and other preexisting changes do not appear as mismatches. The present method of using a hairpin structure takes advantage of the fact that genuine mutations are witnessed in both upper and lower DNA strands while PCR errors occur on one strand at a time. Forcing DNA polymerase to copy both strands in one pass creates 'a double record' of the sequence. Thus, effectively the method boosts the replication fidelity and converts PCR errors, but not other changes to mismatches.

The method of the present invention has wide applicability. For example, polymerase slippage errors produce 'stutter' banding that complicate microsatellite analysis of single[19], or pooled samples[28]. Scanning for very low frequency changes occurring naturally in somatic tissues (<1 mutant in $10^7$ alleles,[1]) or at early stages of carcinogenesis will enable identification of tumor signatures as markers for early tumor detection[6]. Identification of low level mutations in somatic tissues will also facilitate elucidation of carcinogen-specific mutational fingerprints following environmental exposures[17]. Reliable screening for traces of 'onco-mutations'[18,29] can enhance the clinical and diagnostic utility of minimal residual disease detection[30] and the identification of mutations in bodily excretions[31]. For investigating the mechanisms of carcinogenesis, determination of carcinogen-induced mutational spectra in disease-related genes in non-tumorous tissues can provide evidence as to whether a specific mutagenic agent or pathway is involved in a particular disease or cancer. This high-selectivity mutational spectrometry will also help determine whether or not a mutator phenotype must be invoked to explain the acquisition of multiple mutations in tumor cells[18,32].

Most previous studies of mutational spectra were based on phenotypic selection methods (e.g. HPRT, lacZ assays). These methods preclude analysis of genes and human tissues for which selective conditions cannot be devised in in-vitro single cell systems. Molecular methods with selectivity comparable to the spontaneous mutation frequency ($10^{-7}$-$10^{-8}$) that can be applied to all tissues are highly desirable[2, 17]. However, the onset of PCR errors limits several approaches, such as CDCE, which would otherwise have the sensitivity needed to measure the spontaneous mutation frequency[1].

Mutation scanning methods such as DGGE[33] or dHPLC[34] are particularly hampered by PCR errors since, by detecting all possible mutations, they are more likely than RFLP-based methods to encounter misincorporation 'hotspots' which result in false positives. Particularly for mutation detection from limited starting material, such as micrometastatic cells or laser capture microdissected samples, very large DNA amplification is required. The error rate of conventional PCR is then particularly problematic[4] as error containing sequences can comprise >30% of the overall population[27], making it almost impossible to identify genuine mutations. The present method changes that and it allows, for example dHPLC to overcome PCR errors and to perform reliable mutation analysis when starting from a few cells or from minute, laser capture microdissected specimens. RFLP-based methods can now be used to examine few sites for mutations relative to mutation scanning methods.

When a sample is limited, such as in minute LCM-dissected samples, it previously was often not possible to perform more than a single PCR amplification towards the detection of mutations in one gene. With the present method, one can now perform mutation screening in several genes simultaneously from a single sample, for disease gene discovery or diagnostic applications. This 'whole genome' amplification method permits amplification of genomic DNA from small tissue samples in an error-free manner. This allows repeated multi-gene mutation screening from large collections of minute fresh or paraffin-embedded samples without being limited by available starting material or PCR errors.

By removing PCR errors from amplified sequences, the present hairpin-PCR permits the use of well-established techniques such as dHPLC, CDCE, RFLP and microsatellite analysis for detecting traces of mutations in minute biopsies and for investigating the origins of cancer in human tissues without the introduction of polymerase-induced errors.

BRIEF DESCRIPTION OF THE DRAWINGS

In FIG. 1A, the scheme for removing PCR errors following amplification of DNA in a hairpin structure is shown. FIG. 1B shows the expected structure and sequence of hairpin A (SEQ ID NO:1). FIG. 1C shows the expected structure and sequence of hairpin D (SEQ ID NO:2), an oligonucleotide encompassing both top and bottom strands of p53 exon 9.

FIG. 2A, lanes 1-5 show the PCR product of hairpins A,B,C,E, and D, respectively. Lanes 6 and 7 of FIG. 2A show amplification of hairpin D with only forward or only reverse primer. FIG. 2B shows amplification of hairpin C using Advantage Titanium® (lane 1), Pfu Turbo® (lane 3) or Advantage HF2® (lane 5) polymerases respectively; lanes 2, 4 and 6 are water-controls (no template) in each case. FIG. 2C shows quantitative real time PCR of hairpin D: curves 1-4, starting material of 1 ng, 100 pg, 10 pg and 1 pg respectively. FIG. 2D shows hairpin PCR (lanes 1 and 2, in duplicate) followed by denaturation and rapid cooling of the product (lanes 3 and 4, in duplicate). FIG. 2E shows hairpin D amplified with primers that bind the non-complementary ends, and either not extending (lane 1) or extending 9 bases into the hairpin sequence (lane 2). FIG. 2F shows spiking of p53 exon 9-containing hairpin D into 100 ng p53-negative HL-60 genome, followed by hairpin PCR using Advantage Titanium® polymerase. Spiking of 0.01 pg hairpin D corresponds to adding a single p53 exon 9 allele in the genome. Lanes 1-6, hairpin D addition of 0, 0. 1, 1, 10, 100, 1000 pg respectively. FIG. 2G is similar to FIG. 2F, but using Advantage HF2® polymerase. Lanes 1-5, hairpin D addition of 0, 0.01, 0.1, 1, 10 pg. FIG. 2H shows dHPLC-based separation of 1:1 mixtures of homoduplex and heteroduplex hairpins. The threshold of the fraction collector is set on the trailing (slowest) portion of the homoduplex.

FIG. 3A shows the procedure used to convert a native DNA sequence, flanked by two different restriction sites, into a hairpin with non-complementary ends that can be amplified. The hairpin-shaped oligonucleotides Cap1 and Cap2 are ligated to the 5' and 3' of both sequence ends. During hairpin PCR, primers extending into the sequence are used to confer sequence specificity. FIG. 3B shows conversion of a native p53 sequence flanked by Taq I/Alu I sites to a hairpin, followed by hairpin-PCR. Lane 1: Hairpin-PCR product obtained by applying the scheme in FIG. 1A for an isolated p53 sequence. Lane 2: Hairpin-PCR product obtained by applying the scheme in FIG. 1A to human genomic DNA, in order to directly amplify the same Alu I/Taq I target sequence depicted in Lane 1. Lane 3: As in lane 2, but omitting the addition of ligase from scheme FIG. 1A. Lanes 4 and 5: As in lane 2, but omitting the forward or reverse primer, respectively, from PCR.

FIG. 4A depicts a DNA structure with a hairpin at one and non-complementary ends at the other end. FIG. 4B depicts a DNA structure with hairpins at both ends of the double-stranded DNA.

FIG. 6 shows amplification of hairpins using rolling-circle amplification (RCA). The hairpin-shaped oligonucleotide (SEQ ID NO:21) of FIG. 6A was self-ligated to form a closed 'dumbbell-like' structure resembling the structures used for RNA-interference. The dumbbell was then amplified in an isothermal rolling-circle amplification reaction using Phi29 polymerase (from New England Biolabs) and random primers. Following digestion of the RCA product with Alu, the amplified hairpin-dimer DNA was recovered. FIG. 6B shows in lane 1, no Alu digestion; in lane 2, digestion with Alu. The amplification is about 1000-fold. In another example, the hairpin-shaped oligonucleotide (SEQ ID NO:22) of FIG. 6C was self-ligated to form a closed 'dumbbell-like' structure, and then amplified in an isothermal rolling-circle amplification reaction using Phi29 polymerase (from New England Biolabs) and random primers. Following digestion of the RCA product with Nla-III, the amplified hairpin-dimer DNA was recovered.

DETAILED DESCRIPTION OF THE INVENTION

We have discovered compositions and a method to amplify a target nucleic acid sequence, sometimes referred to as the template, that substantially reduces polymerase induced errors in a sequence of interest, and which can supply existing technologies with the necessary 'selectivity leap'. The first step of the method involves converting the sequence of interest into a hairpin, which contains a double stranded region linked at one end through a single stranded loop, and performing PCR on the hairpin-structure. In the second step, the amplified PCR products are heat denatured and rapidly cooled, to convert each amplified PCR product into a hairpin: genuine polymorphisms or mutations will remain fully matched in the hairpin, whereas PCR products which contain a PCR induced error will form a hairpin that contains a mismatch in the double-stranded region. Thereafter, one removes those amplified nucleic acids which contain a mismatch by standard means. This method results in an amplified target nucleic acid which is substantially free of polymerase induced errors.

Figure 4A:
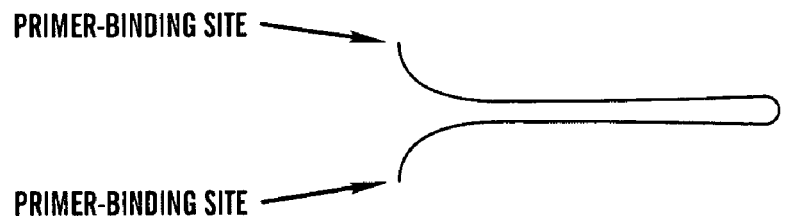
FIGS. 4A and 4B depict two preferred DNA structures.
Figure 4B:
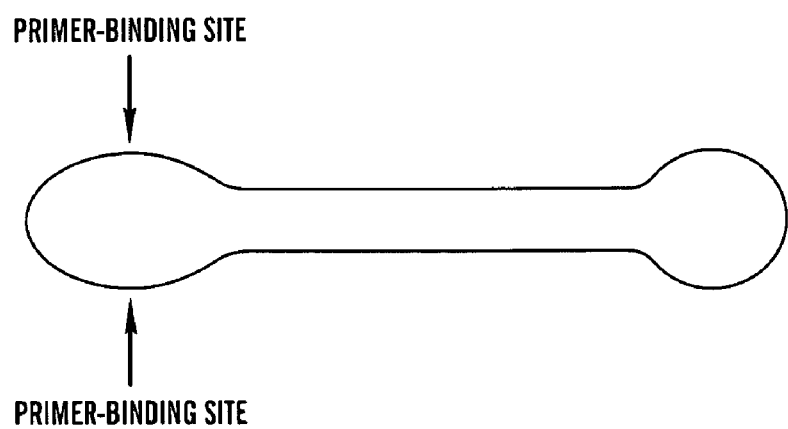

Any method of converting the nucleic acid to a hairpin with non-complementary ends can be used. As used herein, hairpin structures include hairpins and dumbbells. Preferably, one uses oligonucleotide 'caps' which, in a single ligation step allow the conversion of a native DNA sequence to a 'hairpin with non-complementary ends'. For example, one transforms the template nucleic acid, preferably DNA, into a hairpin by capping it at one end, Cap1. Cap1 is sometimes referred to as a 'joining structure,' because once it is ligated to the nucleic acid sequence of interest it joins the upper strand of the nucleic acid sequence of interest to the lower strand of the same nucleic acid molecule. Preferably, one caps the template at the other end, Cap2. Cap 2 is sometimes referred to as a priming structure, because it contains regions of single-stranded nucleic acid to which primers can bind to initiate the polymerization reaction. Caps 1 and 2 naturally form hairpins on their own, to allow their respective ligation to the double stranded DNA ends of the template DNA. In addition, Cap2 contains a region with two non-complementary sequences to allow subsequent primer binding. Finally, Cap2 contains a 'polymerase block' approximately at the center. This 'block' can be one or more synthetic abasic sites; or a deoxynucleotide analogue that does not allow polymerase synthesis; or a uracil that, upon treatment with uracil glycosylase and heating is converted to a strand break, thus effectively providing the 'polymerase block'. Any of the above mentioned polymerase blocks will enable the formation of a 'hairpin with non-complementary ends during the subsequent PCR amplification. See FIG. 4. Alternatively, Cap2 or the priming structure can be a pair of oligonucleotides with are complementary to each other at the ends ligated to the nucleic acid of interest, and non-to each other at their other ends.

In one preferred embodiment of the present invention, unbalanced concentrations of primers are used during PCR ('asymmetric PCR') such that the result of amplification is a single stranded nucleic acid product (i.e. monomer hairpins) instead of a double stranded product (dimer hairpins). In this embodiment, denaturation-renaturation of the DNA is unnecessary.

In contrast to the method developed by Jones et al. (Jones and Winistorfer, 1992) ('panhandle PCR') where the overall structure is in a stem-loop shape but the 'template DNA' is not in a hairpin formation, the present hairpin PCR has the template DNA itself in a hairpin formation. This allows replication of both top and bottom strands of the template in a single pass of the DNA polymerase and subsequent conversion of polymerase errors to mismatches.

Gupte et al., U.S. Pat. Nos. 6,251,610; 6,258,544; and 6,087,099, describe the generation of a DNA hairpin during PCR, by joining top and bottom DNA strands, in order to allow DNA sequencing of both strands in one pass. However, because their procedure requires polymerase extension (i.e. PCR) to generate the DNA strand-joining, it cannot be used to eliminate PCR errors since by the time the two strands are joined together some of the errors can have already occurred. (i.e. since they start by a regular PCR reaction they have already 'lost the game' in step 1).

Oligonucleotide primers useful in the present invention can be synthesized using established oligonucleotide synthesis methods. Methods of synthesizing oligonucleotides are well known in the art. Such methods can range from standard enzymatic digestion followed by nucleotide fragment isolation (see for example, Sambrook, et al., Molecular Cloning: A Laboratory Manual, Second Edition, Cold Spring Harbor, N.Y., (1989), Wu et al, Methods in Gene Biotechnology (CRC Press, New York, N.Y., 1997), and Recombinant Gene Expression Protocols, in Methods in Molecular Biology, Vol. 62, (Tuan, ed., Humana Press, Totowa, N.J., 1997), the disclosures of which are hereby incorporated by reference) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

As used herein, the term "primer" has the conventional meaning associated with it in standard nucleic acid procedures, i.e., an oligonucleotide that can hybridize to a polynucleotide template and act as a point of initiation for the synthesis of a primer extension product that is complementary to the template strand.

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, Biochemistry 34:10807-10815 (1995), McGraw et al., Biotechniques 8:674-678 (1990), and Rychlik et al., Nucleic Acids Res. 18:6409-6412 (1990).

The template nucleic acid that is to be amplified in a hairpin formation is preferably DNA, but it can also be RNA or a synthetic nucleic acid. The template can be of any size, but preferably of a size that can be replicated by DNA or RNA polymerases; most preferably the template in the region 50 bp-1000 base pairs.

The nucleic acid target can be any double stranded nucleic acid which is capable of being amplified.

The target nucleic acid can be from any source, such as a PCR product of a known gene or a preparation of genomic DNA. The preferred target nucleic acid is DNA, but MRNA can also be used. The DNA can be any mixture containing one or various sizes of DNA, such as cDNA synthesized from the whole MRNA collected from cells that need to be screened for mutation/polymorphism; or fractions thereof; or the whole genomic DNA collected from cells that need to be screened for mutation/polymorphism; or fractions thereof; or any combination of the above digested into smaller pieces by enzymes.

Any method of amplifying a nucleic acid target can be used. The amplification reaction can be polymerase chain reaction (PCR), ligase chain reaction (LCR), strand displacement amplification (SDA), transcription mediated amplification (TMA), Qβ-replicase amplification (Q-beta), or rolling circle amplification (RCA).

Preferably, PCR is used to amplify the nucleic acid target.

Any polymerase which can synthesize the desired nucleic acid may be used. Preferred polymerases include but are not limited to Sequenase, Vent, and Taq polymerase. Preferably, one uses a high fidelity polymerase (such as Clontech HF-2) to minimize polymerase-introduced mutations.

In one preferred embodiment, rolling circle amplification (RCA) is used to amplify the nucleic acid template. Rolling circle amplification (RCA) is an isothermal process for generating multiple copies of a sequence. In rolling circle DNA replication in vivo, a DNA polymerase extends a primer on a circular template (Komberg, A. and Baker, T. A. DNA Replication, W. H. Freeman, New York, 1991). The product consists of tandemly linked copies of the complementary sequence of the template. RCA is a method that has been adapted for use in vitro for DNA amplification (Fire, A. and Si-Qun Xu, Proc. Natl. Acad Sci. USA, 1995, 92:4641-4645; Lui, D., et al., J. Am. Chem. Soc., 1996, 118:1587-1594; Lizardi, P. M., et al., Nature Genetics, 1998, 19:225-232; U.S. Pat. No. 5,714,320 to Kool).

In RCA techniques a primer sequence having a region complementary to an amplification target circle (ATC) is combined with an ATC. Following hybridization, enzyme, dNTPs, etc. allow extension of the primer along the ATC template, with DNA polymerase displacing the earlier segment, generating a single stranded DNA product which consists of repeated tandem units of the original ATC sequence. RCA techniques are well known in the art, including linear RCA (LRCA). Any such RCA technique can be used in the present invention.

When RCA is used to amplify the hairpin structure, Cap2 should not contain a polymerase block' in order to allow the enzyme to continuously perform DNA synthesis on the circularized DNA template. In this approach, following ligation of Cap 1 and Cap 2 a polymerase reaction is initiated by addition of a single primer that binds to the Cap 2 non-complementary region. The polymerase then extends the primer by performing numerous circles around the original template, and resulting in a DNA amplification that copies both DNA strands every time it performs a full circle. Similar to non-isothermal amplification, during isothermal amplification too, every time there is a polymerase error during amplification it will form a 'mismatch' while genuine changes such as mutations will be 'fully matched'. Following amplification, the original DNA sequence can be recovered with a restriction digestion which separates the DNA 'caps' introduced in the first step of the procedure.

It is possible that instead of ligating Cap1 and Cap2 to the template DNA for the purpose of generating a hairpin structure with non complementary ends, the same result can be achieved via utilization of the first few steps described in the Gupte et al patents, referred to above. Thus, by using specially designed primers and only the first two PCR cycles, the top and bottom DNA strands become joined. After that, instead of performing further PCR cycling, as the Gupte patent suggests, one proceeds by ligating Cap2 which contains non-complementary ends to the template DNA. Subsequently, hairpin PCR can be performed. The advantage of converting the DNA molecule to a hairpin in this manner is that no Cap1 ligation is required, and that the template DNA sequence does not need to be flanked by two different enzymatic restriction sites anymore. The disadvantage is that, if there is a polymerase-generated error during the 2-cycle initial primer extension, this will not form a mismatch and therefore cannot be eliminated at later stages in the assay. This alternative way of performing hairpin-PCR is simpler and can be useful in some instances where a complete elimination of PCR errors is not required. In fact, if a polymerase with a high-proofreading ability is used, performing just two cycles of PCR should typically not introduce many errors.

Following hairpin PCR, the amplified sequences are denatured and cooled rapidly, so that polymerase errors are converted to mismatches.

Mismatch containing DNA can be eliminated by a number of means known is the art. For example, using a physical separation technique such as size separation or an enzymatic means size separation methods including: Denaturing HPLC (dHPLC); denaturing gradient gel electrophoresis, DGGE; constant denaturant gel electrophoresis, CDGE; constant denaturant capillary electrophoresis, CDCE; heteroduplex analysis (HET)-based gels, etc.

Alternatively, the fraction of DNA molecules containing mismatches can be eliminated or reduced via binding to mismatch-recognizing enzymes. Any known mismatch-binding enzyme can be used. For example, MutS protein; or mismatch-binding glycosylases MutY or TDG; or Cel I; or mismatch-binding endonucleases, or resolvases. In one preferred embodiment, the mismatch-containing DNA is degraded by contact with a combination of a mismatch-binding enzyme (to create a strand break at the mismatch) and exonuclease III (to preferentially degrade the DNA which contains a strand break). A similar degradation of mismatch-containing DNA has previously been reported (Nelson et al., 1993). This procedure will enrich the sample in sequences that do not contain mismatches (PCR errors).

In one preferred embodiment, DNA amplification in a hairpin structure via rolling circle isothermal amplification can be used for RNA interference (RNAi). In this embodiment, nucleic acid molecules in a hairpin structure can be introduced into cells by any known method, for example by direct microinjection or via insertion into a vector and subsequent transfection of cells. In certain cases, these hairpin molecules need to be amplified prior to their microinjection. The direct amplification of hairpin RNAi molecules using the methods of the present application offers practical advantages. Cheng et al., Mol. Genet. Metab. 80: 121-128 (2003); Kittler et al., Sem. Cancer Biol. 13: 259-265 (2003).

Molecular beacon approaches to the specific detection of DNA sequences (Tyagi and Kramer, 1996) require the construction of hairpin-shaped probes that interact with the template sequence during real time PCR. With the hairpin structure of the present method, the template sequence itself is in a hairpin shape, thus it can serve as the molecular beacon, obviating the need for a specific probe. In this approach, the primers used during hairpin-PCR amplification are fluorescently labeled, so that the resulting hairpins are fluorescent and can display the properties of molecular beacons (i.e. fluorescent quenching and de-quenching during amplification).

Figure 5:
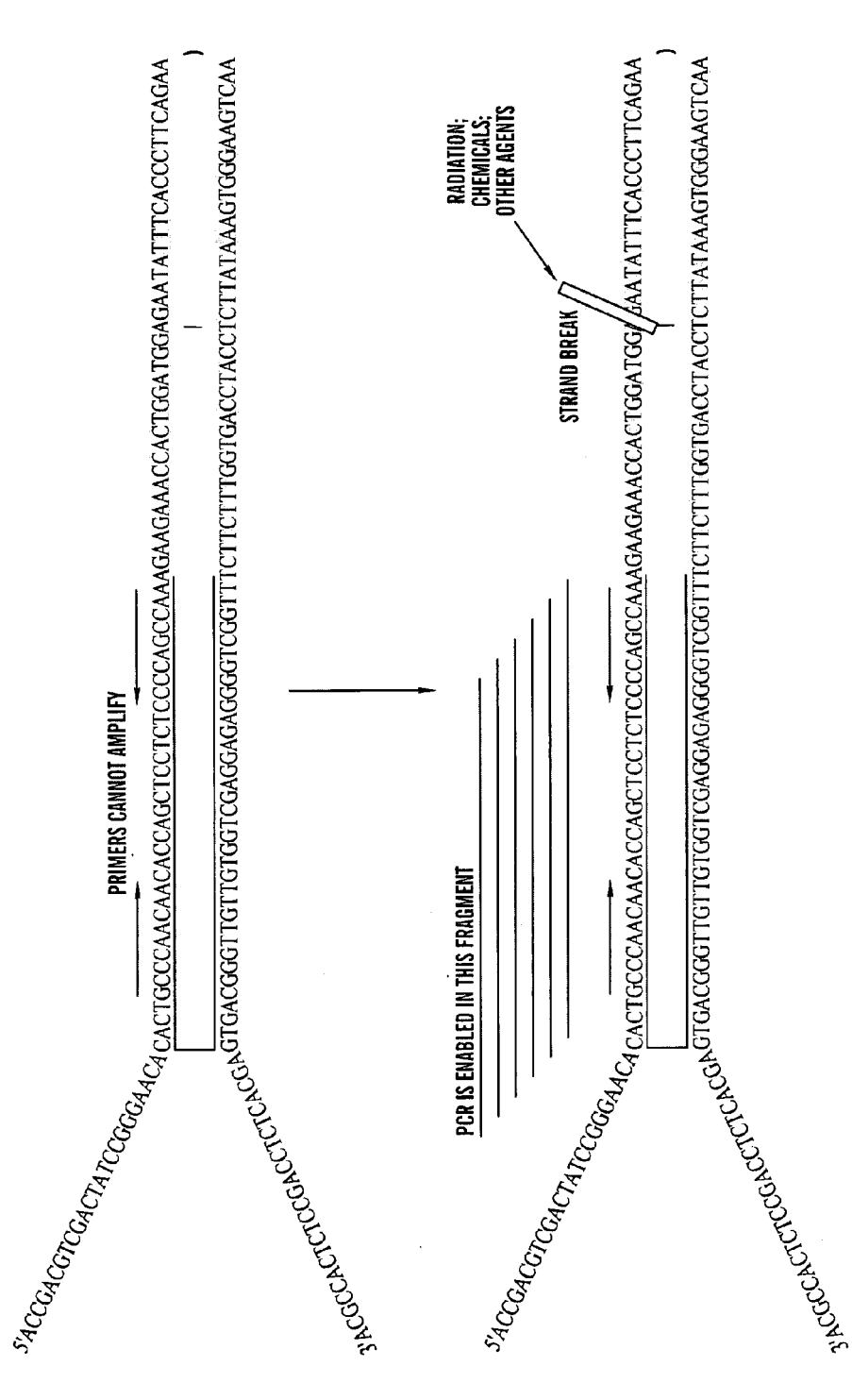
FIG. 5 (SEQ ID NOS 18 & 19-20, respectively) depicts the use of hairpin-shaped DNA as a detector for radiation and/or chemical exposures. The DNA strand breaks off following a strand break anywhere in the shaded area (target), thereby allowing the primers to bind and to PCR amplify the DNA segment. The amount of POR amplification is proportional to how many DNA molecules undergo strand breaks and therefore it can be used to quantify the amount of radiation or chemical agent interacting with the DNA. Finally, the fraction of DNA molecules that remain intact can be re-amplified by using primers binding to the non-complementary linkers, thereby regenerating the original DNA detector molecule.

The method of the present invention can be used to detect DNA damage, for example damage caused by exposure to radiation and chemicals. PCR amplification is suppressed when the primer binding sites are located within a double-stranded nucleic acid, e.g. the hairpin portion of the sequence of interest, but not if primers bind in a single stranded portion of the sequence. This property can allow the nucleic acid hairpins of the present invention to serve as 'radiation/DNA damage detector' molecules. If radiation generates a strand break in certain regions, e.g. the shaded areas in FIG. 5, then a portion of the hairpin breaks-off during PCR, generating two single-stranded pieces of DNA (representing the top strand and the bottom strand in FIG. 5), which are no longer contiguous due to the presence of the DNA damage. Thus, if PCR is performed on a hairpin structure using two primers which are complementary to sequences on the top strand of the hairpin, then in the absence of DNA damage, the region remains double stranded and the primers cannot bind or amplify the DNA, but in the presence of even a small amount of DNA damage, the top strand is now single stranded, which allows primer binding and PCR amplification. The amount of PCR product produced is proportional to the radiation dose or to the DNA damage induced. In this embodiment, any agent can be included which protects against the generation of spontaneous strand breaks, which can be induced by the heating and cooling applied during PCR. For example, to avoid any heating-generated strand breaks, hydroxylamine can be added to the PCR reaction to prevent heat-generated abasic sites from becoming strand breaks.

Because the hairpin contains also the non-complementary linkers, the radiation dosimeter can be replicated at will by the methods described above, thus providing 'infinite' amounts of starting material. By miniaturizing and arraying many PCR reaction chambers one can obtain an entire profile of radiation doses over an area (i.e. resulting in a 'radiation imaging' device). Finally, because nucleic acid such as DNA is part of every cell in the body, it is possible to utilize for example the DNA as an intrinsic probe for measuring radiation or chemical exposures ('biodosimetry'). In this approach, following radiation/chemical exposure DNA will be extracted from cells, digested, and converted to a hairpin shape. One can use multiple primer sites depending upon the size of the starting template. If the radiation/chemical exposure resulted in a strand break, appropriate placement of the PCR primers should yield a product, while if there is no strand break no product will be produced. The ability to convert DNA to a dosimeter, combined with the DNA functionality should also allow in-vivo targeting of molecular regions with this dosimeter.

The oligonucleotide primers of the present invention can be coupled to any molecule of interest (e.g. an indicator fluorescent molecule) using any method which allows the primer and the molecule of interest to be coupled. In one preferred embodiment, the N-terminal amino acid of each molecule is cysteine, and the oligonucleotides carry a thiol group at the 3' or 5' end, to allow coupling to the N-terminal cysteine.

One preferred molecule of interest is an indicator fluorescent molecule.

Coupling may be accomplished by any chemical reaction that will bind the molecule to the primer so long as the primer remains able to bind the hybridization site in the nucleic acid target and form a duplex, allowing PCR amplification. This linkage can include many chemical mechanisms, for instance covalent binding, affinity binding, intercalation, coordinate binding and complexation. The preferred binding is, however, covalent binding. For example, for a protein, covalent binding can be achieved either by direct condensation of existing side chains or by the incorporation of external bridging molecules. Many bivalent or polyvalent linking agents are useful in coupling protein molecules to other molecules such as the primers of the present invention. For example, representative coupling agents can include organic compounds such as thioesters, carbodiimides, succinimide esters, disocyanates, glutaraldehydes, diazobenzenes and hexamethylene diamines. This listing is not intended to be exhaustive of the various classes of coupling agents known in the art but, rather, is exemplary of the more common coupling agents (see Killen and Lindstrom, *J. Immunol*. 133:1335-2549, 1984; Jansen, F. K., et al., *Imm. Rev*. 62:185-216, 1982; and Vitetta et al., supra).

Preferred linkers are described in the literature. See, for example, Ramakrishnan, S., et al., *Cancer Res*. 44: 201-208 (1984), describing the use of MBS (M-maleimidobenzoyl-N-hydroxysuccinimide ester). See also Umemoto et al., U.S. Pat. No. 5,030,719, describing the use of a halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. (21558G); (iii) SPDP (succinimidyl-6[3-(2-pyridyldithio) propionamido] hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In one preferred embodiment, the molecules are proteins which contain an N-terminal cysteine, which can be coupled to an oligonucleotide carrying a thiol group at either the 3' or 5' end and a donor or acceptor at the 5' or 3' end, respectively. In this embodiment it is desirable to substitute any other cysteines in the protein to other amino acids.

In another preferred embodiment, the present invention provides kits suitable for amplifying a nucleic acid of interest to generate a substantially error-free amplified product. Said kits comprise at least a single stranded first and second non-complementary nucleic acid for ligation to the first end of the double stranded nucleic acid of interest, or a cap of single stranded nucleic acid, where the cap contains a sequence midway in the cap (such as an abasic site) that cannot be amplified by PCR, and where the sequences on either side of this sequence are non-complementary. Said kits also comprise a cap for ligation to the second end of the double stranded nucleic acid of interest, such that the upper and lower strands of the nucleic acid are contiguous, creating the hairpin structure. The kit further comprises two primers for amplification of the hairpin, as described above. Such kits may optionally include the reagents required for performing amplification reactions, such as DNA polymerase, DNA polymerase cofactors, and deoxyribonucleotide-5'-triphosphates. Optionally, the kit may also include various polynucleotide molecules, DNA or RNA ligases, restriction endonucleases, reverse transcriptases, terminal transferases, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure.

PCR-based amplification is used in almost every aspect of genetic diagnosis, DNA cloning, mutation detection and basic research. The present method can reduce the number of PCR associated errors by at least 1-2 orders of magnitude. Thus, one can now use PCR based techniques, to identify cancer cells at an early stage (Sidransky et al., 1997), to detect mutations in single cells (Liu et al., 2002) or to reliably identify minimal residual disease (Bartram et al., 1990). Previously, in all these applications, polymerase misincorporations invariably became disguised as mutations and result to false positives (Reiss et al., 1990).

EXAMPLES

Example 1

Figure 1A:
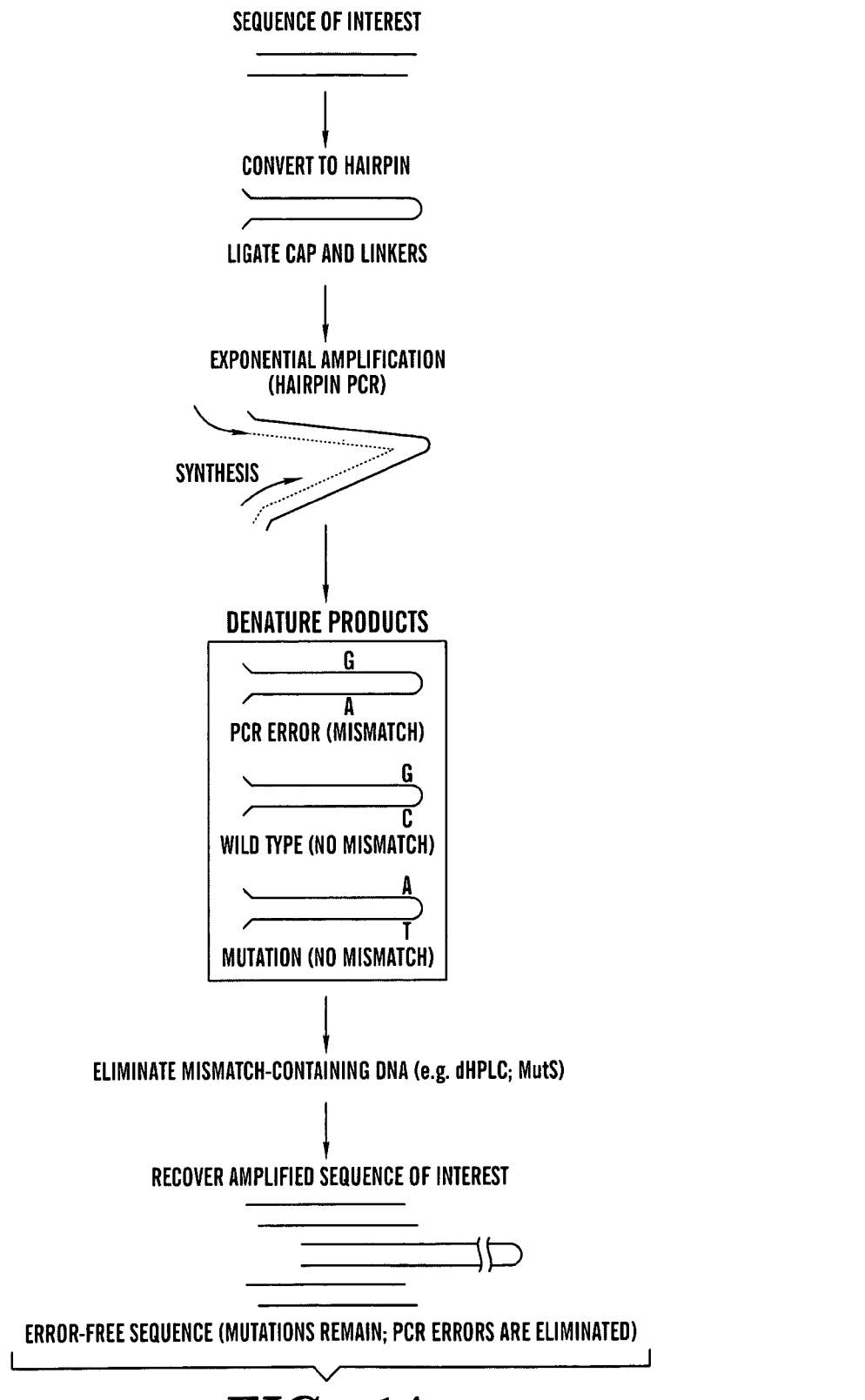
FIGS. 1A-1C outline the generation of error-free amplified DNA via hairpin PCR.
Figure 1B:
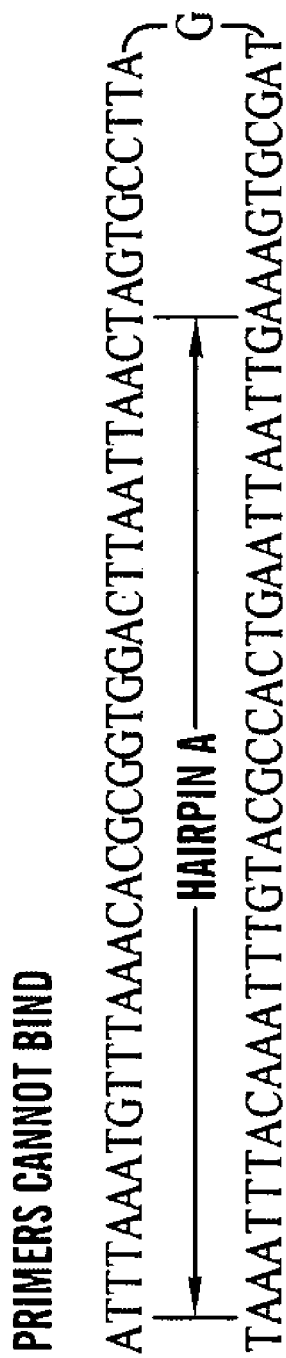
Figure 1C:
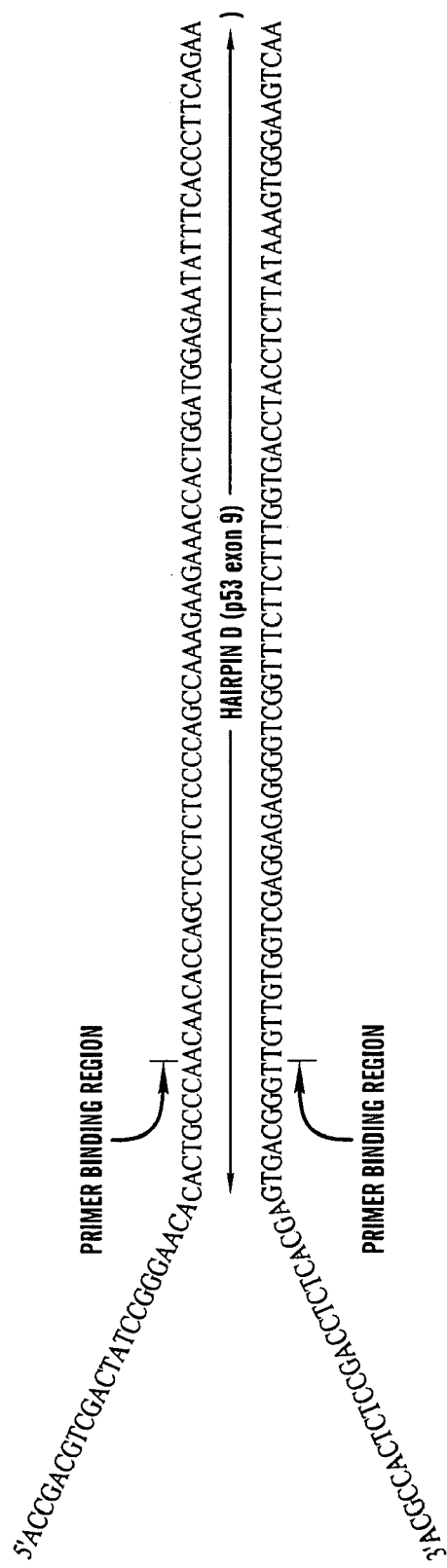

Amplification of Hairpins Using Polymerase Chain Reaction (PCR) Hairpin-Forming, Long Oligonucleotides Five long oligonucleotides expected to form hairpins were synthesized by Oligos Etc and HPLC-purified (Oregon, USA). The sequence of hairpins A and D (SEQ ID NOs:1 and 2, respectively) are depicted in FIGS. 1B-C. Sequences of hairpin B (SEQ ID NO:3), hairpin C (SEQ ID NO:4), and hairpin E (SEQ ID NO:5), which were designed to contain non-complementary ends like hairpin D, were:

```
Hairpin B:
5' ACC GAC GTC GAC TAT CCG GGA    (SEQ ID NO:3)

ACA CAT GAT TTA AAT GTT TAA ACA

CGC GGT GGA CTT AAT TAA CTA GTG

CCT TAG GTA GCG TGA AAG TTA ATT

AAG TCA CCG CAT GTT TAA ACA TTT

AAA TGT ACA GCA CTC TCC AGC CTC

TCA CCG CA 3';

Hairpin C:
5' ACC GAC GTC GAC TAT CCG GGA    (SEQ ID NO:4)

ACA CAA GAT TTA AAT GTT TAA ACA

CGC GGT GAC TTA ACA GGC GCG CCT
```

-continued

```
TAA CTA GTG CCT TAG GTA GCG TGA

AAG TTA AGG CGC GCC TGT TAA GTC

ACC GCG TGT TTA AAC ATT TAA ATC

TTG AGC ACT CTC CAG CCT CTC ACC

GCA 3';

Hairpin E:
5' ACC GAC GTC GAC TAT CCG GGA    (SEQ ID NO:5)

ACA GAT CCA TGC ACT GCC CAA CAA

CAC CAG CTC CTC TCC CCA GCC AAA

GAA GAA ACC ACT GGA TGG AGA ATA

TTT CGA CCC TTC AGA AAA CTG AAG

GGT CGA AAT ATT CTC CAT CCA GTG

GTT TCT TCT TTG GCT GGG GAG AGG

AGC TGG TGT TGT TGG GCA GTG CAT

GGA TCA GCA CTC TCC AGC CTC TCA

CCG CA 3'.
```

Hairpin-PCR

Designated amounts of hairpins B-D were used in a 25 µl PCR reaction using Titanium Advantage® polymerase (Clontech, Palo Alto, Calif.) and forward primer 5'-GTG AGA GGC TGG AGA GTG CT-3' (SEQ ID NO:6); and reverse primer 5'-ACG TCG ACT ATC CGG GAA CA-3' (SEQ ID NO:7). PCR thermo-cycling conditions were: 94°, 30 sec; (94°, 30 sec/68°, 60 sec)×25 cycles; 68°, 60 sec; 4°; Hold. The PCR products were then examined via ethidium-stained agarose gel electrophoresis. Alternatively, PCR amplification was conducted using high fidelity Advantage HF-2$^R$ polymerase (Clontech) or Pfu Turbo® (Strategene Inc). In addition, using the same thermocycling conditions, quantitative real time PCR in the presence of SYBR Green I dye was performed in a Cepheid I SmartCycler™ machine. Primers used for PCR of hairpin A were forward primer 5' TAA ATG TTT AAA CAC GCG GT 3' (SEQ ID NO:8); and reverse primer 5' TAA ATG TTT AAA CAT GCG GT 3' (SEQ ID NO:9). To amplify picogram amounts of hairpin D spiked into 100 ng human genomic DNA from HL-60 cells, touchdown PCR was applied: 94°, 30 sec; (94°, 20 sec/65°, 20 sec/68°, 20 sec)×30 cycles, with annealing temperature decreasing 1°/cycle; (94°, 10 sec/55°, 20 sec/68°, 20 sec)×15 cycles; 68°, 6 min; 4°; Hold.

dHPLC Analysis of Olizonucleotide Hairpins

To perform separation of mixtures of heteroduplex and homoduplex hairpins, 1 ng hairpins were injected into a WAVE™ dHPLC system (Transgenomics Inc, Cambridge, Mass.) and run under denaturing conditions at different temperatures, following the company-supplied protocol (see Transgenomics et al., www.transgenomics.com). The dHPLC system was equipped with a fraction collector that allows selection of the elution product according to the DNA retention time on the dHPLC column.

Conversion of Native DNA Sequences to a Hairpin, and PCR Amplification

The forward primer 5'AGG CCT TCA TGA CTG ATA CCA 3' (SEQ ID NO:10) and reverse primer 5' TGA GAT CGA CTG AGA CCC CAA 3' (SEQ ID NO:11) were used to amplify from genomic DNA a 137 bp p53 sequence (nucleotides 2215-2352 of Genbank sequence #X54156) flanked by Taq I and Alu I restriction sites near each end. Following double digestion of this sequence with Taq I (65° C., 1 h) and Alu I (37° C., 1 h) the restricted p53 DNA fragment was purified via QIAquick™ centrifugation columns (Qiagen Inc, Valencia, Calif.) and then ligated to the hairpin-shaped sequences Cap1 (SEQ ID NO:12): 5' (phosphate)-CGACG-GCGCGCCGCCTTAGGTAGCGTTAGGCGCGCCGT-3', which ligates Taq I sites; and Cap2 (SEQ ID NO:13), 5' (phosphate)-CTGCCGAGTTCCTGCTTTGAGATGCTGT-TGAGUUACGTCGACTATCCTTGAAC ACCAACTCG-GCAG-3' which ligates Alu I (blunt) sites, following the protocol described by Horie and Shimada (Horie et al., 1994). Briefly, ligation of the two caps to DNA was performed by adding a 100-fold molar excess of each Cap into 10 µM DNA template in the presence of T4 DNA polymerase and incubating the 50 µl reaction volume overnight at 15° C. 2 µl ligation mixture were then treated with uracil glycosylase (Roche Diagnostics), at 37° C., 30 min, in the company-supplied buffer, 20 µl final volume, in a PCR tube. Upon addition of PCR components and buffer, a reaction was carried out using Titanium polymerase for 35 cycles and the following thermocycling conditions: 94°, 30 sec; (94°, 30 sec/68°, 60 sec)× 25 cycles; 68°, 60 sec; 4°; Hold. Primers that bind the ligated Cap2 and overlap the target p53 sequence by 12 bases were used in this PCR reaction: forward primer (SEQ ID NO:14) 5' ATGAGATGGGGTCAGCTGCCTTCATCG-GCGCGCCCATGATTT 3'; and reverse primer (SEQ ID NO:15) CTTCTCCCCCTCCTCTGTTGCTCATCG-GCGCGCC 3'.

Next, the same p53 sequence flanked by Taq I and Alu I sites was converted to a hairpin and amplified from human genomic DNA. 1 µg human genomic DNA from an osteosarcoma cell line (ATCC CRL-1543) was digested with Taq I, purified and then digested with Alu I. The protocol described above was used to ligate, treat with uracil glycosylase and PCR amplify the target sequence from digested genomic DNA using the same primers and thermocycling conditions. PCR products were examined via ethidium stained gel electrophoresis. Amplified sequences were then excised from the gel (QIAquick™ gel extraction kit, Qiagen Inc.), and sequenced via dideoxy-sequencing at the Dana Farber Molecular Biology Core Facility. The primer used for sequencing were the same with those used during the hairpin PCR reaction.

RESULTS AND DISCUSSION

Amplification of DNA Hairpins With Non-Complementary Ends

The observation that, if DNA is amplified in a hairpin structure mismatches should be almost always separated from mutations urged the development of hairpin PCR. Indeed, if the polymerase introduces an A>G mutation on the upper DNA strand it is unlikely that, during synthesis of the bottom strand of a single hairpin it will perform the exact opposite error (T>C mutation) at the same position of the complementary strand. Even for a polymerase with a large error rate of $10^{-4}$/base the odds for a double-error event are $10^{-4} \times 10^{-4} \times 0.25 = 2.5 \times 10^{-9}$, i.e. less than the expected spontaneous mutation rate in somatic tissues (Khrapko et al., 1994). On the other hand, practically all genuine mutations should remain fully matched following hairpin-PCR, as these reside in both strands from the beginning (FIG. 1A). This complete discrimination of polymerase errors from the mutations should allow subsequent isolation of error-free amplified hairpins by one of many strategies, such as dHPLC (Xiao et al., 2001), CDCE (Khrapko et al., 1994), DGGE (Cariello et al., 1991) or enzymatic depletion of mismatches using mismatch recognition proteins, MutS (Smith et al., 1997), MutY (Chakrabarti et al., 2000), TDG (Pan et al., 2002).

Figure 2A:
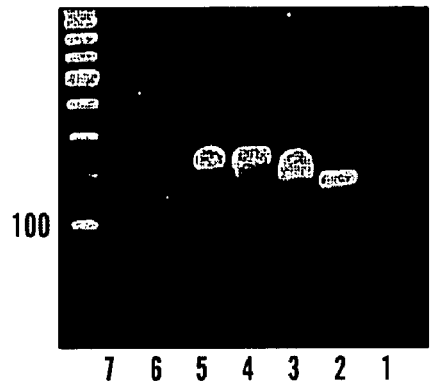
FIGS. 2A-2H show PCR amplification and dHPLC separation of hairpin-shaped oligonucleotides.
Figure 2B:
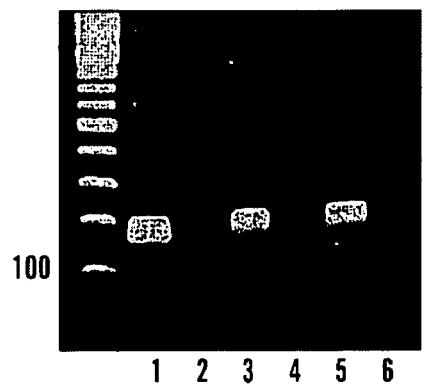
Figure 2C:
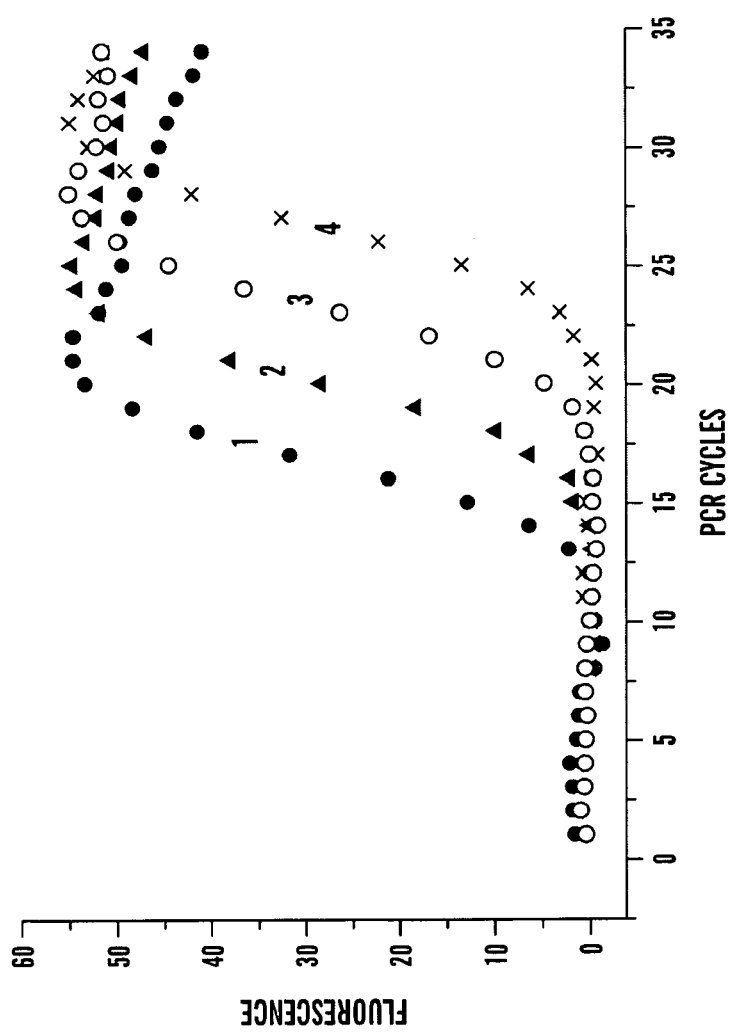
Figure 2D:
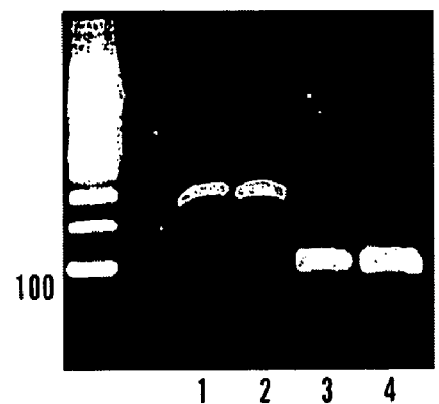
Figure 2E:
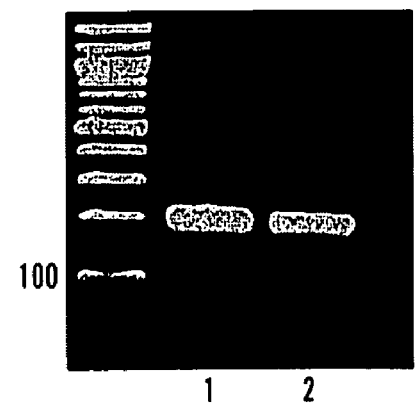

To confirm the basic technical aspects of this approach, we designed long oligonucleotides (B,C,D,E, 149, 168, 200, and 218 nucleotides respectively) expected to form hairpins with non-complementary ends which do not inhibit primer binding at their ends (FIG. 1C), as well as a regular hairpin A, 131 bp, which lacks the non-complementary ends (FIG. 1B), for comparison. Hairpins D and E encompass the complete sequence of p53 exon 9. 1 ng each hairpin was then used in a 25 µl PCR reaction using Titanium Advantage® polymerase and primers designed to operate on the non-complementary ends of hairpins B-D, or alternatively on the complementary ends of hairpin A. Hairpins B-D produce a PCR product, while hairpin A does not (FIG. 2A, lanes 1-5). The data indicate that hairpins are readily amplified as long as primers are allowed to bind, and the polymerase is able to synthesize the hairpin complement, presumably by displacing the opposite strand. Omission of either forward or reverse primers abolishes the product (FIG. 2A, lanes 6-7) which indicates that amplification requires both primers and that the full length hairpin is replicated by the polymerase. Hairpin PCR was repeated using two proof-reading polymerases, Pfu Turbo™, or Advantage-HF2 and amplification was obtained (FIG. 2B). FIG. 2C depicts quantitative real-time hairpin-PCR profiles of hairpin D serial dilutions, using SYBR Green I dye. The exponential nature of amplification is evident. Because of the way hairpin-PCR operates (FIG. 1A), the PCR products are expected to result to double-stranded DNA molecules, each strand of which is a full hairpin. To separate the two strands, and to recover the original hairpins, following purification of the PCR product the samples are denatured at 95° C., 1 min, and rapidly cooled by placing them directly on ice. This procedure does not allow time for substantial cross-hybridization of different DNA strands, while each strand is expected to rapidly form a hairpin due to its self-complementary sequence. FIG. 2D demonstrates that rapid cooling converts the hairpin amplification product (lanes 1 and 2) to a band approximately half the size (lanes 3 and 4), which corresponds to the expected monomer hairpin. Next, the forward and reverse primers used for the amplifications in FIG. 2A were re-designed to encompass an additional 9 nucleotide extension (20+9=29mers) inside the p53 exon 9 hairpin D sequence. FIG. 2E demonstrates that, although the 3'-end of the primers falls within the hairpin portion of the sequence, amplification remains almost unhindered. The data are consistent with the occurrence of primer binding by means of the 20 base overlap with the non-complementary end of the hairpin, and that the 3' end of the primers temporarily displaces the hairpin sequence. This 'invasion' by hybridized oligonucleotides at the DNA ends, also reported by Guilfoyle et al. (1997), presumably happens frequently enough to allow polymerase binding and primer extension to occur. Therefore restricting the primers on the non-complementary ends amplifies every hairpin sequence that contain those ends, while using primers with 3' ends extending into the hairpin sequence renders hairpin-PCR sequence specific.

Figure 2F:
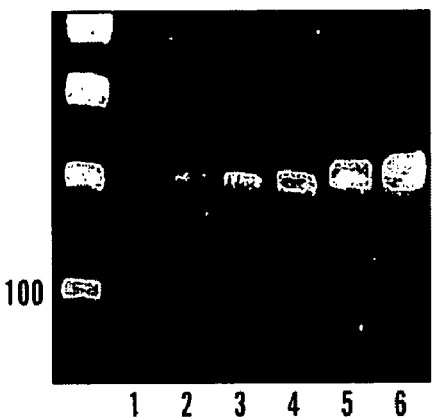
Figure 2G:
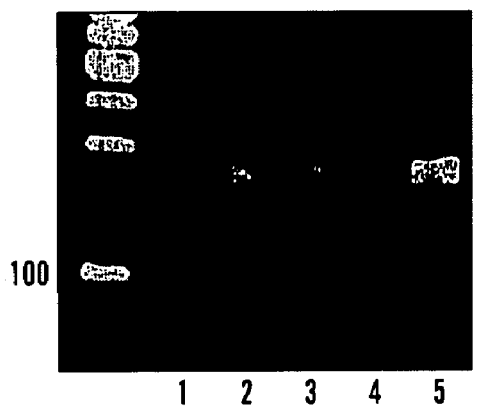

To investigate the amplification efficiency of hairpin PCR, 100 ng purified human genomic DNA from a cell line that lacks the p53 gene (HL-60 cells), was mixed with decreasing amounts of the p53 exon 9-containing hairpin D. One human genome (~$3 \times 10^9$ bp), is ~$1.5 \times 10^7$ times the size of hairpin D therefore spiking $10^{-2}$ pg hairpin D into 100 ng genomic DNA is approximately equivalent to adding a single copy p53 exon 9 in a hairpin formation in the genome. FIGS. 2F and 2G demonstrate hairpin PCR amplification of p53 exon 9 using two different polymerases. Amplification from 0.01-0.1 pg hairpin D in the presence of genomic DNA is obtained. The amplification efficiency of hairpin PCR appears comparable to that of regular PCR.

DHPLC Separation of Homoduplex From Heteroduplex Hairpins

To confirm that hairpins containing a single base mismatch, such as those expected to result from polymerase misincorporations, can be distinguished from fully-matched hairpins via dHPLC, we injected homoduplex hairpin D into a WAVE™ dHPLC system equipped with a fraction collector. Two more hairpins were synthesized. These were identical to the homoduplex hairpin except that they were synthesized to contain sequence changes, 56G>A (SEQ ID NO:16) or 46insACA (SEQ OD NO:17), respectively

```
5' ACC GAC GTC GAC TAT CCG GGA    SEQ ID NO: 16

ACA CAA GAT TTA AAT GTT TAA ACA

CAC GGT GAC TTA ACA GGC GCG CCT

TAA CTA GTG CCT TAG GTA GCG TGA

AAG TTA AGG CGC GCC TGT TAA GTC

ACC GCG TGT TTA AAC ATT TAA ATC

TTG AGC ACT CTC CAG CCT CTC ACC

GCA 3';

5' ACC GAC GTC GAC TAT CCG GGA    SEQ ID NO: 17

ACA CAA GAT TTA AAT GTT TAA ACA

ACA CAC GGT GAC TTA ACA GGC GCG

CCT TAA CTA GTG CCT TAG GTA GCG

TGA AAG TTA AGG CGC GCC TGT TAA

GTC ACC GCG TGT TTA AAC ATT TAA

ATC TTG AGC ACT CTC CAG CCT CTC

ACC GCA 3'.
```

Figure 2H:
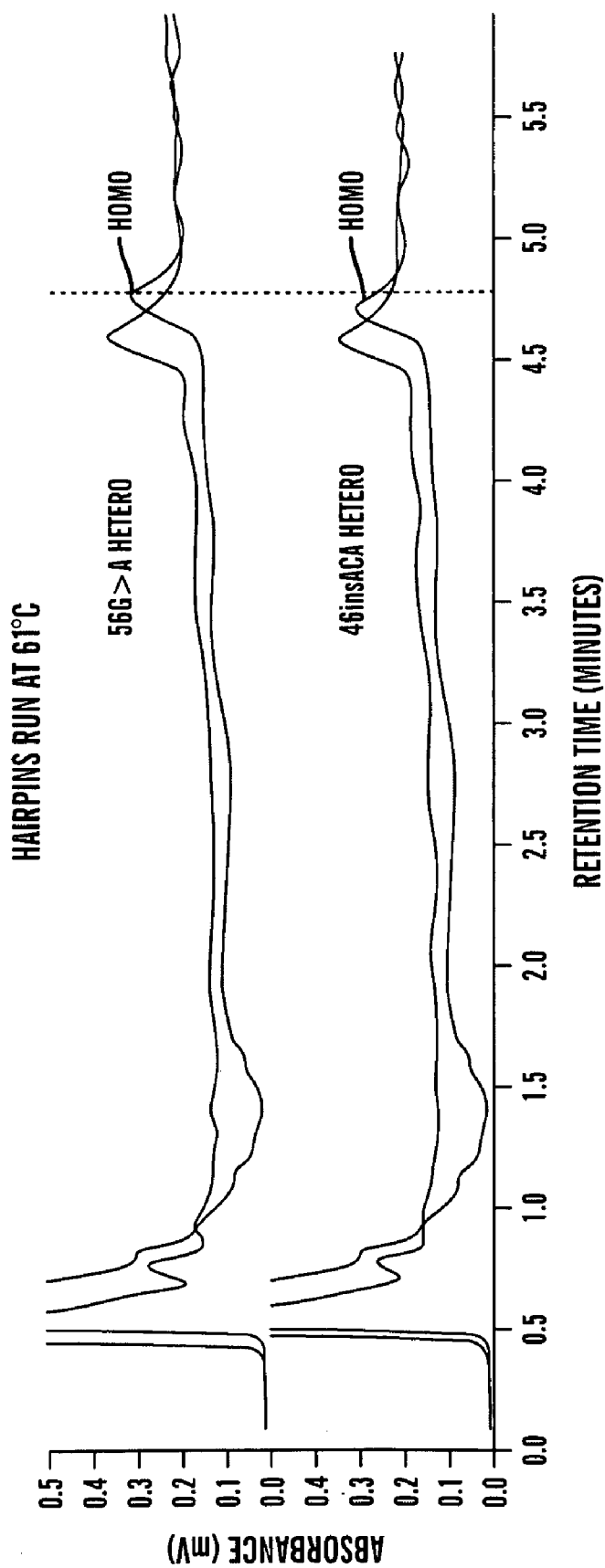

Upon folding, these hairpins form mismatches which simulate a potential misincorporation by Taq polymerase (Smith et al., 1997) and a Taq slippage error (Perlin et al., 1995), respectively. 1 ng each heteroduplex and homoduplex hairpin was injected separately into dHPLC, or, alternatively, mixed (1:1) and injected as a mixture. At a partially denaturing temperature of 61° C., the peaks from the heteroduplex hairpins could be distinguished from the fully-matched, homoduplex hairpin, FIG. 2H. Setting the threshold of the fraction collector on the trailing part of the homoduplex peak allows the collection of mainly (70-80%) homoduplex hairpin out of this mixture. This example simulated a worse case scenario, where the heteroduplex DNA was 50% of the overall sample. Normally however, the heteroduplex peak resulting from PCR errors will be a smaller fraction (~1-10%) of the homoduplex peak (Wright et al., 1990). From the data in FIG. 2H it can be estimated that if PCR errors are confined to 10% or 1% of the sequences, one would collect >95% and >99% homoduplex DNA respectively, resulting to a radical elimination of heteroduplex hairpins from the mixtures. In dHPLC chromatography almost all possible base changes and PCR errors are detectable (Transgenomics, www.transgenomic.com), however individual base changes can result to varying degrees of separation of heteroduplexes from the homoduplex peak (Xiao et al., 2001). Nevertheless, homoduplex DNA tends to have the longest retention time on the column (Xiao et al., 2001). By re-cycling the collected homoduplex through the dHPLC for a second time and by collecting the trailing portion of the homoduplex each time should practically filter-out the misincorporations.

Conversion of Native DNA Sequences to Hairpins and PCR Amplification

Figure 3A:
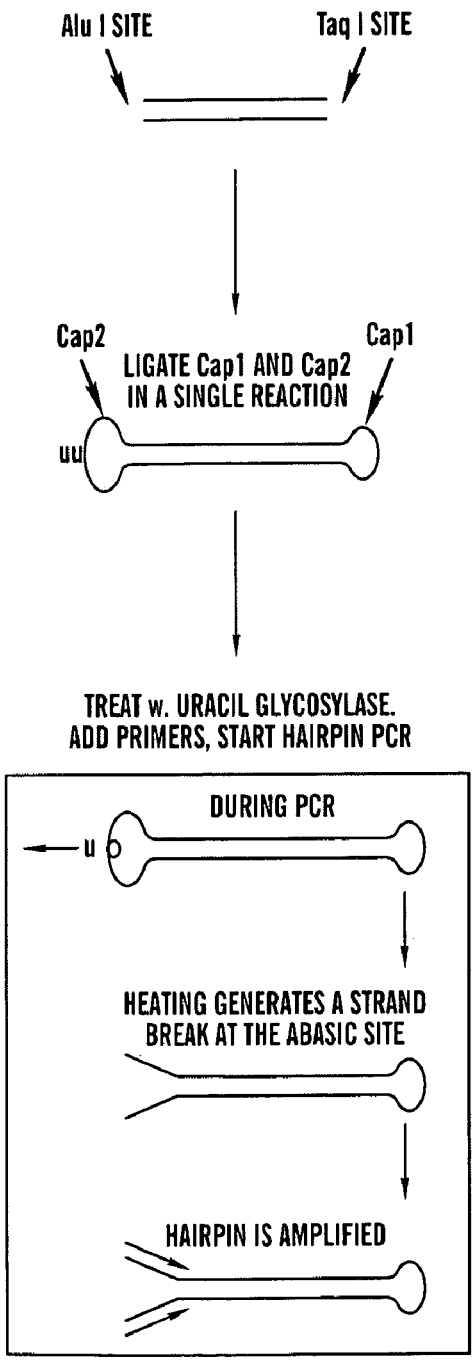
FIGS. 3A-3B show conversion of a DNA sequence to a hairpin and PCR amplification.
Figure 3B:
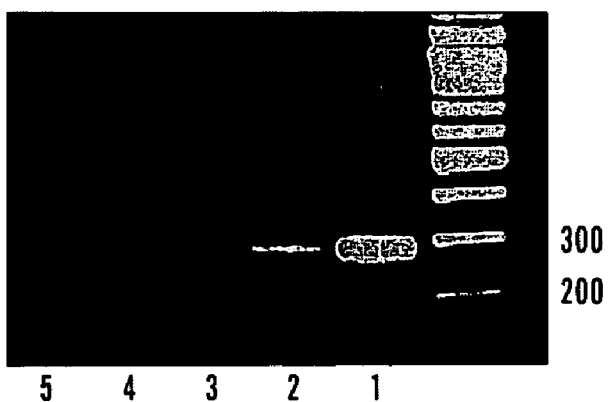

To enable the scheme in FIG. 1A, conversion of a native DNA fragment to a hairpin that can be amplified directly from human genomic DNA is required. To convert a sequence to a hairpin with non-complementary ends we performed ligation of two different oligonucleotide 'caps', Cap1 and Cap2, at the positions of two restriction sites encompassing the sequence (FIG. 3A). Cap1 and Cap2 are small oligonucleotides designed to form a hairpin that ligates both top and bottom strands at the respective DNA restriction site (Horie et al., 1994). In addition, Cap2 contains two centrally-located uracils. Following the simultaneous ligation of both caps at the two DNA ends, a treatment with uracil glycosylase removes the uracils and generates abasic sites at the center of Cap2. During the heating step of the subsequent PCR reaction the glycosylase is inactivated and a strand break is expected to form via beta elimination at the abasic sites (Longo et al., 1990) which allows the hairpin to obtain a structure that can be PCR-amplified. To demonstrate the application, a 91 bp p53 sequence flanked by Alu I and Nla-III restriction sites was generated following a double digestion of a larger DNA fragment which had been first amplified from genomic DNA using regular PCR. Following ligation of caps 1 and 2, the resulting 145 bp fragment was amplified using primers overlapping the non-complementary linkers and the p53 sequence itself. A ~290 bp double stranded product was observed (FIG. 3B, lane 1).

Next, human genomic DNA expected to generate the same Alu I/Taq I-flanked p53 fragment following a double enzymatic digestion was subjected to the same procedure. A ~290 bp was generated when the full scheme of FIG. 3A was applied (FIG. 3B, lane 2) but not when DNA ligase was omitted (FIG. 3B, lane 3) or when a single primer was used in the hairpin-PCR reaction (FIG. 3B, lanes 4 and 5). The DNA fragment was then excised from the gel and sequenced. Sequencing verified that the correct sequence had been amplified and that the expected hairpin structure of the amplified sequence had formed.

Both unknown and known mutation detection methods are affected by PCR errors and the most selective methods are those that are affected most. The principal limitation for mutation scanning via constant denaturant capillary electrophoresis (CDCE) is the fidelity of the polymerase used (Keohavong et al., 1989; Andre et al., 1997). High selectivity mutation scanning via DGGE and dHPLC is ultimately limited by polymerase error rate (Keohavong et al., 1989; Transgenomics, www.transgenomic.com; Cariello et al., 1991). Some of the high selectivity assays for RFLP-based known mutation detection (PCR/RE/LCR (Wilson et al., 2000); Radioactivity-based PCR-RFLP (Nakazawa et al., 1990); RSM (Steingrimsdottir et al., 1996; Jenkins et al., 1998); APRIL-ATM (Kaur et al., 2002) and others reviewed in Parsons et al., 1997, utilize PCR in at least one stage prior to RFLP-selection. Therefore these are also limited by PCR errors (McKinzie et al., 2001). The ability to amplify DNA without being limited by polymerase-introduced errors would significantly impact mutation detection and cancer diagnosis. A mismatch-binding protein, MutS, was previously used to deplete mismatches caused by PCR errors, in order to improve DNA synthesis fidelity (Smith et al., 1997). However, low frequency genuine mutations are also converted to mismatches and eliminated in this process, thus there is no benefit to mutation detection. In contrast hairpin PCR converts polymerase errors to mismatches while also retains mutations in the homoduplex DNA. Forcing the enzyme to keep a double record of the sequence effectively boosts the DNA replication fidelity, as it is unlikely that a misincorporation will happen at the same position in both DNA strands simultaneously. We demonstrated amplification of small (75-145 bp) sequences in hairpin formation. However polymerases can displace much longer (>1 kb) DNA stretches during synthesis (Lizardi et al., 1998). With appropriate adaptation it is possible to amplify large genomic fractions in a hairpin formation. Accordingly, a genome-wide depletion of PCR errors will allow accurate genome-wide genotyping from limited starting material.

We have demonstrated that DNA hairpins designed to have non-complementary ends are efficiently PCR amplified and that dHPLC can discriminate among homoduplex and heteroduplex hairpins. Native DNA sequences can be converted to a hairpin structure and amplified from human genomic DNA.

Example 2

Amplification of Hairpins Using Rolling-Circle Amplification

Figures 6C, 6D:
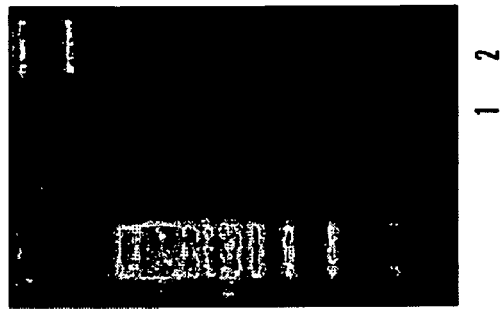
FIG. 6D shows in lane 1, no digestion Nla-III; lane 1: with Nla-III digestion). The amplification is about 500-fold.

FIG. 6 shows amplification of hairpins using rolling-circle amplification (RCA). The hairpin-shaped oligonucleotide of FIG. 6A was self-ligated to form a closed 'dumbbell-like' structure resembling the structures used for RNA-interference. The dumbbell was then amplified in an isothermal rolling-circle amplification reaction using Phi29 polymerase (from New England Biolabs) and random primers. Following digestion of the RCA product with Alu, the amplified hairpin-dimer DNA was recovered. FIG. 6B shows in lane 1, no Alu digestion; in lane 2, digestion with Alu. The amplification is about 1000-fold. In another example, the hairpin-shaped oligonucleotide of FIG. 6C was self-ligated to form a closed 'dumbbell-like' structure, and then amplified in an isothermal rolling-circle amplification reaction using Phi29 polymerase (from New England Biolabs) and random primers. Following digestion of the RCA product with Nla-III, the amplified hairpin-dimer DNA was recovered. FIG. 6D shows in lane 1, no digestion Nla-III; lane 1: with Nla-III digestion). The amplification is about 500-fold.

REFERENCES

1. Li-Sucholeiki, X. C. & Thilly, W. G. A sensitive scanning technology for low frequency nuclear point mutations in human genomic DNA. *Nucleic Acids Res* 28, E44. (2000).

2. Khrapko, K. et al. Mutational spectrometry without phenotypic selection: human mitochondrial DNA. *Nucleic Acids Res* 25, 685-693. (1997).

3. Jackson, A. L. & Loeb, L. A. On the origin of multiple mutations in human cancers. *Semin Cancer Biol* 8, 421-429 (1998).

4. Liu, Q., Swiderski, P. & Sommer, S. S. Truncated amplification: a method for high-fidelity template-driven nucleic acid amplification. *Biotechniques* 33, 129-132, 134-126, 138. (2002).

5. Bartram, C. R., Yokota, S., Hansen-Hagge, T. E. & Janssen, J. W. Detection of minimal residual leukemia by polymerase chain reactions. *Bone Marrow Transplant* 6 Suppl 1, 4-8 (1990).

6. Sidransky, D. Nucleic acid-based methods for the detection of cancer. *Science* 278, 1054-1059 (1997).

7. Keohavong, P. & Thilly, W. G. Fidelity of DNA polymerases in DNA amplification. *Proc Natl Acad Sci USA* 86, 9253-9257. (1989).

8. Andre, P., Kim, A., Khrapko, K. & Thilly, W. G. Fidelity and mutational spectrum of Pfu DNA polymerase on a human mitochondrial DNA sequence. *Genome Res* 7, 843-852. (1997).

9. Cariello, N. F., Swenberg, J. A. & Skopek, T. R. Fidelity of *Thermococcus litoralis* DNA polymerase (Vent) in PCR determined by denaturing gradient gel electrophoresis. *Nucleic Acids Res* 19, 4193-4198 (1991).

10. Transgenomics, I. Transgenomic Optimase™ Polymerase Delivers Highest Fidelity in PCR for WAVE® System Analysis (US). http://www.transgenomic.com/pdf/AN119u.pdf (2002).

11. Wilson, V. L. et al. Oncogenic base substitution mutations in circulating leukocytes of normal individuals. *Cancer Res* 60, 1830-1834. (2000).

12. Parsons, B. L. & Heflich, R. H. Detection of basepair substitution mutation at a frequency of $1 \times 10(-7)$ by combining two genotypic selection methods, MutEx enrichment and allele-specific competitive blocker PCR. *Environ Mol Mutagen* 32, 200-211 (1998).

13. Nakazawa, H., Aguelon, A. M. & Yamasaki, H. Relationship between chemically induced Ha-ras mutation and transformation of BALB/c 3T3 cells: evidence for chemical-specific activation and cell type-specific recruitment of oncogene in transformation. *Mol Carcinog* 3, 202-209 (1990).

14. Steingrimsdottir, H. et al. Development of new molecular procedures for the detection of genetic alterations in man. *Mutat Res* 353, 109-121. (1996).

15. Jenkins, G. J., Chaleshtori, M. H., Song, H. & Parry, J. M. Mutation analysis using the restriction site mutation (RSM) assay. *Mutat Res* 405, 209-220. (1998).

16. Kaur, M. et al. Ligation of a primer at a mutation: a method to detect low level mutations in DNA. *Mutagenesis* 17, 365-374. (2002).

17. Parsons, B. L. & Heflich, R. H. Genotypic selection methods for the direct analysis of point mutations. *Mutat Res* 387, 97-121 (1997).

18. McKinzie, P. B., Delongchamp, R. R., Heflich, R. H. & Parsons, B. L. Prospects for applying genotypic selection of somatic oncomutation to chemical risk assessment. *Mutat Res* 489, 47-78. (2001).

19. Perlin, M. W., Lancia, G. & Ng, S. K. Toward fully automated genotyping: genotyping microsatellite markers by deconvolution. *Am J Hum Genet* 57, 1199-1210 (1995).

20. Tyagi, S. & Kramer, F. R. Molecular beacons: probes that fluoresce upon hybridization. *Nat Biotechnol* 14, 303-308 (1996).

21. Tyagi, S., Marras, S. A. & Kramer, F. R. Wavelength-shifting molecular beacons. *Nat Biotechnol* 18, 1191-1196 (2000).

22. Ennis, P., Zemmour, J., Salter, R. & Parham, P. Rapid Cloning of HLA-A,B cDNA by Using the Polymerase Chain Reaction: Frequency and Nature of Errors Produced in Amplification. *PNAS* 87, 2833-2837 (1990).

23. Kaur, M. & Makrigiorgos, G. M. Novel amplification of DNA in a hairpin structure: a strategy for elimination of PCR errors from amplified DNA.—Submitted for publication.

24. Khrapko, K., Andre, P., Cha, R., Hu, G. & Thilly, W. G. Mutational spectrometry: means and ends. *Prog Nucleic Acid Res Mol Biol* 49, 285-312 (1994).

25. Cariello, N. F. & Skopek, T. R. Mutational analysis using denaturing gradient gel electrophoresis and PCR. *Mutat Res* 288, 103-112. (1993).

26. Cariello, N. F., Swenberg, J. A., De Bellis, A. & Skopek, T. R. Analysis of mutations using PCR and denaturing gradient gel electrophoresis. *Environ Mol Mutagen* 18, 249-254 (1991).

27. Smith, J. & Modrich, P. Removal of polymerase-produced mutant sequences from PCR products. *Proc Natl Acad Sci USA* 94, 6847-6850 (1997).

28. Daniels, J. et al. A simple method for analyzing microsatellite allele image patterns generated from DNA pools and its application to allelic association studies. *Am J Hum Genet* 62, 1189-1197 (1998).

29. Wilson, V. L. et al. Needle-in-a-haystack detection and identification of base substitution mutations in human tissues. *Mutat Res* 406, 79-100 (1999).

30. van Houten, V. M. et al. Molecular assays for the diagnosis of minimal residual head-and-neck cancer: methods, reliability, pitfalls, and solutions. *Clin Cancer Res* 6, 3803-3816. (2000).

31. Dong, S. M. et al. Detecting colorectal cancer in stool with the use of multiple genetic targets. *J Natl Cancer Inst* 93, 858-865. (2001).

32. Christians, F. C., Newcomb, T. G. & Loeb, L. A. Potential sources of multiple mutations in human cancers. *Prev Med* 24, 329-332 (1995).

33. McKinzie, P. B., Delongchamp, R. R., Heflich, R. H., and Parsons, B. L. Prospects for applying genotypic selection of somatic oncomutation to chemical risk assessment. Mutat Res, 489: 47-78, 2001.

34. Liu, W., Smith, D. I., Rechtzigel, K. J., Thibodeau, S. N. & James, C. D. Denaturing high performance liquid chromatography (DHPLC) used in the detection of germline and somatic mutations. *Nucleic Acids Res* 26, 1396-1400. (1998).

35. Jones D H, Winistorfer S C (1992) Sequence specific generation of a DNA panhandle permits PCR amplification of unknown flanking DNA. Nucleic Acids Res 20: 595-600

36. Nelson S F, McCusker J H, Sander M A, Kee Y, Modrich P, Brown P O (1993) Genomic mismatch scanning: a new approach to genetic linkage mapping [see comments]. Nat Genet 4: 11-8

37. Tyagi S, Kramer F R (1996) Molecular beacons: probes that fluoresce upon hybridization. Nat Biotechnol 14: 303-8

38. Fujimura, F. K., Northrup, H., Beaudet, A. L., and O'Brien, W. E. Genotyping errors with the polymerase chain reaction. N Engl J Med, 322: 61, 1990.

39. Wright, P. A. and Wynford-Thomas, D. The polymerase chain reaction: miracle or mirage? A critical review of its uses and limitations in diagnosis and research. J Pathol, 162: 99-117, 1990.

40. Keohavong, P. and Thilly, W. G. Fidelity of DNA polymerases in DNA amplification. Proc Natl Acad Sci U S A, 86: 9253-9257, 1989.

41. Ennis, P., Zemmour, J., Salter, R., and Parham, P. Rapid Cloning of HLA-A,B cDNA by Using the Polymerase Chain Reaction: Frequency and Nature of Errors Produced in Amplification. PNAS, 87: 2833-2837, 1990.

42. Liu, Q., Swiderski, P., and Sommer, S. S. Truncated amplification: a method for high-fidelity template-driven nucleic acid amplification. Biotechniques, 33: 129-132, 134-126, 138, 2002.

43. Perlin, M. W., Lancia, G., and Ng, S. K. Toward fully automated genotyping: genotyping microsatellite markers by deconvolution. Am J Hum Genet, 57: 1199-1210, 1995.

44. Parsons, B. L. and Heflich, R. H. Genotypic selection methods for the direct analysis of point mutations. Mutat Res, 387: 97-121, 1997.

45. Khrapko, K., Coller, H., Andre, P., Li, X. C., Foret, F., Belenky, A., Karger, B. L., and Thilly, W. G. Mutational spectrometry without phenotypic selection: human mitochondrial DNA. Nucleic Acids Res, 25: 685-693, 1997.

46. Sidransky, D. Nucleic acid-based methods for the detection of cancer. Science, 278: 1054-1059, 1997.

47. Bartram, C. R., Yokota, S., Hansen-Hagge, T. E., and Janssen, J. W. Detection of minimal residual leukemia by polymerase chain reactions. Bone Marrow Transplant, 6 Suppl 1: 4-8, 1990.

48. Reiss, J., Krawczak, M., Schloesser, M., Wagner, M., and Cooper, D. N. The effect of replication errors on the mismatch analysis of PCR-amplified DNA. Nucleic Acids Res, 18: 973-978, 1990.

49. Diatchenko, L., Lau, Y. F., Campbell, A. P., Chenchik, A., Moqadam, F., Huang, B., Lukyanov, S., Lukyanov, K., Gurskaya, N., Sverdlov, E. D., and Siebert, P. D. Suppression subtractive hybridization: a method for generating differentially regulated or tissue-specific cDNA probes and libraries. Proc Natl Acad Sci USA, 93: 6025-6030, 1996.

50. Transgenomics, I. Single Nucleotide Polymorphism (SNP), Insertion & Deletion on the WAVE® Nucleic Acid Fragment Analysis System. http://www.transgenomic.com/pdf/AN112.pdf, 2002.

51. Horie, K. and Shimada, K. Gene targeting by a vector with hairpin-shaped oligonucleotide caps. Biochem Mol Biol Int, 32: 1041-1048, 1994.

52. Khrapko, K., Andre, P., Cha, R., Hu, G., and Thilly, W. G. Mutational spectrometry: means and ends. Prog Nucleic Acid Res Mol Biol, 49: 285-312, 1994.

53. Li-Sucholeiki, X. C. and Thilly, W. G. A sensitive scanning technology for low frequency nuclear point mutations in human genomic DNA. Nucleic Acids Res, 28: E44, 2000.

54. Xiao, W. and Oefner, P. J. Denaturing high-performance liquid chromatography: A review. Hum Mutat, 17: 439-474, 2001.

55. Khrapko, K., Hanekamp, J. S., Thilly, W. G., Belenkii, A., Foret, F., and Karger, B. L. Constant denaturant capillary electrophoresis (CDCE): a high resolution approach to mutational analysis. Nucleic Acids Res, 22: 364-369, 1994.

56. Cariello, N. F., Swenberg, J. A., De Bellis, A., and Skopek, T. R. Analysis of mutations using PCR and denaturing gradient gel electrophoresis. Environ Mol Mutagen, 18: 249-254, 1991.

57. Smith, J. and Modrich, P. Removal of polymerase-produced mutant sequences from PCR products. Proc Natl Acad Sci USA, 94: 6847-6850, 1997.

58. Chakrabarti, S., Price, B. D., Tetradis, S., Fox, E. A., Zhang, Y., Maulik, G., and Makrigiorgos, G. M. Highly selective isolation of unknown mutations in diverse DNA fragments: toward new multiplex screening in cancer. Cancer Res, 60: 3732-3737, 2000.

59. Pan, X. and Weissman, S. M. An approach for global scanning of single nucleotide variations. Proc Natl Acad Sci USA, 99: 9346-9351, 2002.

60. Guilfoyle, R. A., Leeck, C. L., Kroening, K. D., Smith, L. M., and Guo, Z. Ligation-mediated PCR amplification of specific fragments from a class-II restriction endonuclease total digest. Nucleic Acids Res, 25: 1854-1858, 1997.

61. Transgenomics, I. Transgenomic Optimase™ Polymerase Delivers Highest Fidelity in PCR for WAVE® System Analysis (US); http://www.transgenomic.com/pdf/AN119u.pdf, 2002.

62. Longo, M. C., Beminger, M. S., and Hartley, J. L. Use of uracil DNA glycosylase to control carry-over contamination in polymerase chain reactions. Gene, 93: 125-128, 1990.

63. Andre, P., Kim, A., Khrapko, K., and Thilly, W. G. Fidelity and mutational spectrum of Pfu DNA polymerase on a human mitochondrial DNA sequence. Genome Res, 7: 843-852, 1997.

64. Cariello, N. F., Swenberg, J. A., and Skopek, T. R. Fidelity of *Thermococcus litoralis* DNA polymerase (Vent) in PCR determined by denaturing gradient gel electrophoresis. Nucleic Acids Res, 19: 4193-4198, 1991.

65. Wilson, V. L., Yin, X., Thompson, B., Wade, K. R., Watkins, J. P., Wei, Q., and Lee, W. R. Oncogenic base substitution mutations in circulating leukocytes of normal individuals. Cancer Res, 60: 1830-1834, 2000.

66. Nakazawa, H., Aguelon, A. M., and Yamasaki, H. Relationship between chemically induced Ha-ras mutation and transformation of BALB/c 3T3 cells: evidence for chemical-specific activation and cell type-specific recruitment of oncogene in transformation. Mol Carcinog, 3: 202-209, 1990.

67. Steingrimsdottir, H., Beare, D., Cole, J., Leal, J. F., Kostic, T., Lopez-Barea, J., Dorado, G., and Lehmann, A. R. Development of new molecular procedures for the detection of genetic alterations in man. Mutat Res, 353: 109-121, 1996.

68. Jenkins, G. J., Chaleshtori, M. H., Song, H., and Parry, J. M. Mutation analysis using the restriction site mutation (RSM) assay. Mutat Res, 405: 209-220, 1998.

69. Kaur, M., Zhang, Y., Liu, W. H., Tetradis, S., Price, B. D., and Makrigiorgos, G. M. Ligation of a primer at a mutation: a method to detect low level mutations in DNA. Mutagenesis, 17: 365-374, 2002.

70. Myers, R. M., Lumelsky, N., Lerman, L. S. & Maniatis, T. Detection of single base substitutions in total genomic DNA. *Nature* 313, 495-498 (1985).

71. Lizardi, P. M., Huang, X., Zhu, Z., Bray-Ward, P., Thomas, D. C., and Ward, D. C. Mutation detection and single-molecule counting using isothermal rolling-circle amplification. Nat Genet, 19: 225-232, 1998.

All references described herein are incorporated by reference.

I claim:

1. A method of amplifying a hairpin structure comprising converting a double stranded nucleic acid into the hairpin structure, wherein the double stranded nucleic acid contains at least one sequence of interest, and is referred to as a template nucleic acid, and wherein the template nucleic acid has an upper strand with a 5' and a 3' end and a lower strand with a 5' and a 3' end, the method comprising:

(a) ligating a first single stranded nucleic acid to the 5' end of the upper strand of the template nucleic acid,
    (b) ligating a second single stranded nucleic acid, which is non-complementary to the first single stranded nucleic acid to the 3' end of the lower strand of the nucleic acid,
    (c) ligating a cap of single stranded nucleic acid to both the 5' end of the lower strand and the 3' end of the upper strand of the template nucleic acid, such that the 3' end of the upper strand and the 5' end of the lower strand are contiguous, thereby creating the hairpin structure;

and further comprising performing polymerase chain reaction with a first primer that binds to at least a portion of the upper single stranded non-complementary region at the 5' end of the upper strand, and a second primer that binds to at least a portion of the lower single stranded non-complementary region at the 3' end of the lower strand.

2. A method of amplifying a nucleic acid sequence of interest that generates a PCR-amplified product which is substantially free of polymerase-induced errors, comprising:

(a) providing a sequence of interest comprising a double stranded nucleic acid, referred to as a template nucleic acid, wherein the template nucleic acid has an upper strand with a 5' and a 3' end and a lower strand with a 5' and a 3' end,
    (b) converting the nucleic acid sequence of interest into a first hairpin DNA structure by ligating a first single stranded nucleic acid to the 5' end of the upper strand of the template nucleic acid, ligating a second single stranded nucleic acid, which is non-complementary to the first single stranded nucleic acid to the 3' end of the lower strand of the nucleic acid, and ligating a cap of a single stranded nucleic acid to both the 5' end of the lower strand and the 3' end of the upper strand of the template nucleic acid, such that the 3' end of the upper strand and the 5' end of the lower strand are contiguous, thereby creating the first hairpin structure;
    (c) amplifying the first hairpin DNA structure using PCR with a first primer that binds to at least a portion of the first single stranded nucleic acid, and a second primer that binds to at least a portion of the second single stranded nucleic acid to produce a plurality of linear double stranded PCR products, wherein the double stranded PCR product comprises an amplified sequence of interest and its complementary sequence flanked 5' and 3' by the first and the second single-stranded nucleic acid sequences;
    (d) converting the linear double stranded PCR products into a plurality of second hairpin structures by a method which induces denaturation of the linear double stranded PCR products into single stranded PCR products, followed by sudden renaturation, wherein the amplified sequence of interest and its complement within each single strand hybridize during renaturation, thereby forming a hairpin structure;
    (e) identifying from the second hairpin structures mismatch containing hairpin structures that comprise gaps in binding between the sequence of interest and its complementary sequence in the double-stranded region of the second hairpin structure wherein the gaps are a result of polymerase-generated nucleotide changes, insertions, or deletions, and
    (f) removing such mismatch containing hairpin structure, and collecting the DNA that contains no mismatches.

3. The method of claim 2, wherein the method which induces denaturation followed by sudden renaturation is selected from the group consisting of (a) heat denaturation followed by rapid cooling, (b) addition of sodium hydroxide followed by sudden neutralization of the solution, and (c) addition of formamide followed by sudden removal of formamide.

4. The method of claim 2, wherein the mismatch containing hairpin structures that contain PCR-induced errors and that have a mismatch in the double stranded region are separated from hairpin DNAs which do not contain mismatches by a method which recognizes DNA containing a mismatch.

5. The method of claim 4, wherein the method which recognizes DNA containing mismatches is selected from the group consisting of dHPLC-mediated fraction collection, denaturing gradient gel electrophoresis (DGGE), constant denaturant gel electrophoresis (CDGE), constant denaturant capillary electrophoresis (CDCE), and an enzymatic-based separation method.

6. The method of claim 5, wherein the enzymatic-based separation method is performed either in solution or bound to a solid support, and the enzyme is at least one enzyme selected from the group consisting of mismatch-recognition enzymes MutS, MutY, and TDG; Cel I; resolvases; endonuclease V; cleavases, and exonucleases.

7. The method of claim 2, wherein concentration of the first and the second primer in step (b) is equal to each other.

8. The method of claim 2, wherein concentration of the first and the second primer in step (b) is unbalanced.

9. The method of claim 4 further comprising an assay consisting of mutation detection, mutation analysis, polymorphism detection, polymorphism analysis, microsatellite analysis, cloning, and protein functional analysis of the separated hairpin DNAs which do not contain mismatches.

10. The method of claim 9, wherein the method of mutation or polymorphism detection is selected from the group consisting of PCR, PCR/RE/LCR, MutEx-ACB-PCR, RFLP analysis, and APRIL-ATM.

* * * * *

SEQUENCE LISTING

<160> NUMBER OF SEQ ID NOS: 22

<210> SEQ ID NO 1
<211> LENGTH: 92
<212> TYPE: DNA
<213> ORGANISM: Artificial Sequence
<220> FEATURE:

-continued

```
<223> OTHER INFORMATION: Description of Artificial Sequence: Synthetic
      oligonucleotide

<400> SEQUENCE: 1
atttaaatgt taaacacgc ggtggactta attaactagt gccttagtag cgtgaaagtt      60
aattaagtca ccgcatgttt aaacatttaa at                                   92

<210> SEQ ID NO 2
<211> LENGTH: 200
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
accgacgtcg actatccggg aacacactgc ccaacaacac cagctcctct ccccagccaa     60
agaagaaacc actggatgga gaatatttca cccttcagaa aactgaaggg tgaaatattc    120
tccatccagt ggtttcttct ttggctgggg agaggagctg gtgttgttgg gcagtgagca    180
ctctccagcc tctcaccgca                                                200

<210> SEQ ID NO 3
<211> LENGTH: 149
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
accgacgtcg actatccggg aacacatgat ttaaatgttt aaacacgcgg tggacttaat     60
taactagtgc cttaggtagc gtgaaagtta attaagtcac cgcatgttta aacatttaaa    120
tgtacagcac tctccagcct ctcaccgca                                      149

<210> SEQ ID NO 4
<211> LENGTH: 168
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
accgacgtcg actatccggg aacacaagat ttaaatgttt aaacacgcgg tgacttaaca     60
ggcgcgcctt aactagtgcc ttaggtagcg tgaaagttaa ggcgcgcctg ttaagtcacc    120
gcgtgtttaa acatttaaat cttgagcact ctccagcctc tcaccgca                 168

<210> SEQ ID NO 5
<211> LENGTH: 218
<212> TYPE: DNA
<213> ORGANISM: Artificial Sequence
<220> FEATURE:
<223> OTHER INFORMATION: Description of Artificial Sequence: Primer

<400> SEQUENCE: 5
accgacgtcg actatccggg aacagatcca tgcactgccc aacaacacca gctcctctcc     60
ccagccaaag aagaaaccac tggatggaga atatttcgac ccttcagaaa actgaagggt    120
cgaaatattc tccatccagt ggtttcttct ttggctgggg agaggagctg gtgttgttgg    180
gcagtgcatg gatcagcact ctccagcctc tcaccgca                            218
```

```
<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
gtgagaggct ggagagtgct                                            20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
acgtcgacta tccgggaaca                                            20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
taaatgttta aacacgcggt                                            20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
taaatgttta aacatgcggt                                            20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 10
aggccttcat gactgatacc a                                          21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 11
tgagatcgac tgagacccca a                                          21

<210> SEQ ID NO 12
<211> LENGTH: 38
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 12
cgacggcgcg ccgccttagg tagcgttagg cgcgccgt                                38

<210> SEQ ID NO 13
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
ctgccgagtt cctgctttga gatgctgttg aguuacgtcg actatccttg aacaccaact    60
cggcag                                                                66

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 14
atgagatggg gtcagctgcc ttcatcggcg cgcccatgat tt                         42

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 15
cttctccccc tcctctgttg ctcatcggcg cgcc                                  34

<210> SEQ ID NO 16
<211> LENGTH: 168
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
accgacgtcg actatccggg aacacaagat ttaaatgttt aaacacacgg tgacttaaca    60
ggcgcgcctt aactagtgcc ttaggtagcg tgaaagttaa ggcgcgcctg ttaagtcacc   120
gcgtgtttaa acatttaaat cttgagcact ctccagcctc tcaccgca                168

<210> SEQ ID NO 17
<211> LENGTH: 171
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
accgacgtcg actatccggg aacacaagat ttaaatgttt aaacaacaca cggtgactta    60
```

-continued

```
acaggcgcgc cttaactagt gccttaggta gcgtgaaagt taaggcgcgc ctgttaagtc    120
accgcgtgtt taaacattta aatcttgagc actctccagc ctctcaccgc a             171
```

<210> SEQ ID NO 18
<211> LENGTH: 199
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

```
accgacgtcg actatccggg aacacactgc ccaacaacac cagctcctct ccccagcaaa    60
gaagaaacca ctggatggag aatatttcac ccttcagaaa actgaagggt gaaatattct    120
ccatccagtg gtttcttctt tggctgggga gaggagctgg tgttgttggg cagtgagcac    180
tctccagcct ctcaccgca                                                 199
```

<210> SEQ ID NO 19
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

```
accgacgtcg actatccggg aacacactgc ccaacaacac cagctcctct ccccagccaa    60
agaagaaacc actggatgg                                                 79
```

<210> SEQ ID NO 20
<211> LENGTH: 119
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

```
aatatttcac ccttcagaaa actgaagggt gaaatattct ccatccagtg gtttcttctt    60
tggctgggga gaggagctgg tgttgttggg cagtgagcac tctccagcct ctcaccgca    119
```

<210> SEQ ID NO 21
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

```
ctgccgagtt cctgctttga gatgctgttg agacgtcgac tatccttgaa caccaactcg    60
gcag                                                                 64
```

<210> SEQ ID NO 22
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

-continued

```
atttaaatgt ttaaacacgc ggtgacttaa caggcgcgcc ttaactagtg ccttaggtag      60
cgtgaaagtt aaggcgcgcc tgttaagtca ccgcgtgttt aaacatttaa atcatg        116
```